(12) United States Patent
Yen

(10) Patent No.: US 10,056,561 B2
(45) Date of Patent: *Aug. 21, 2018

(54) ORGANIC MATERIAL AND ORGANIC ELECTROLUMINESCENT DEVICE USING THE SAME

(71) Applicant: LUMINESCENCE TECHNOLOGY CORPORATION, Hsin-Chu (TW)

(72) Inventor: Feng-Wen Yen, Taipei (TW)

(*) Notice: Subject to any disclaimer, the term of this patent is extended or adjusted under 35 U.S.C. 154(b) by 238 days.

This patent is subject to a terminal disclaimer.

(21) Appl. No.: 14/957,604

(22) Filed: Dec. 3, 2015

(65) Prior Publication Data

US 2016/0190470 A1    Jun. 30, 2016

Related U.S. Application Data

(63) Continuation-in-part of application No. 14/585,219, filed on Dec. 30, 2014.

(51) Int. Cl.

| H01L 51/50 | (2006.01) |
|---|---|
| H01L 51/00 | (2006.01) |
| C09K 11/06 | (2006.01) |
| C07D 251/24 | (2006.01) |
| C09K 11/02 | (2006.01) |
| C07D 239/26 | (2006.01) |
| C07D 403/14 | (2006.01) |
| C07D 403/04 | (2006.01) |
| C07D 209/86 | (2006.01) |
| C07D 333/76 | (2006.01) |
| C07D 307/91 | (2006.01) |

(52) U.S. Cl.
CPC ........ *H01L 51/0067* (2013.01); *C07D 209/86* (2013.01); *C07D 239/26* (2013.01); *C07D 251/24* (2013.01); *C07D 307/91* (2013.01); *C07D 333/76* (2013.01); *C07D 403/04* (2013.01); *C07D 403/14* (2013.01); *C09K 11/02* (2013.01); *C09K 11/06* (2013.01); *H01L 51/0056* (2013.01); *H01L 51/0072* (2013.01); *H01L 51/0073* (2013.01); *H01L 51/0074* (2013.01); *C09K 2211/185* (2013.01); *H01L 51/0081* (2013.01); *H01L 51/0085* (2013.01)

(58) Field of Classification Search
None
See application file for complete search history.

(56) References Cited

U.S. PATENT DOCUMENTS

| 8,962,160 B2 | 2/2015 | Yen et al. |
|---|---|---|
| 8,993,130 B2 | 3/2015 | Yen et al. |
| 9,048,437 B2 | 6/2015 | Yen et al. |

(Continued)

FOREIGN PATENT DOCUMENTS

| WO | 2008062636 A1 | 5/2008 |
|---|---|---|
| WO | 2012091471 A2 | 7/2012 |

*Primary Examiner* — Gregory D Clark

(57) ABSTRACT

The present invention discloses an novel organic material containing indenotriphenylene derivatives and organic EL device using the indenotriphenylene derivatives as hole blocking layer(HBL), electron transport layer(ETL) and/or phosphorescent host can efficiently lower driving voltage, lower power consumption and increase the efficiency. The present invention further relates to the methods of preparation for the indenotriphenylene derivatives and organic EL device comprising these derivatives.

16 Claims, 1 Drawing Sheet

(56) References Cited

U.S. PATENT DOCUMENTS

| | | | |
|---|---|---|---|
| 9,172,046 B1* | 10/2015 | Kim | H01L 51/0056 |
| 2012/0280632 A1* | 11/2012 | Kim | H05B 33/0815 |
| | | | 315/192 |
| 2013/0048975 A1 | 2/2013 | Hong et al. | |
| 2014/0151645 A1 | 6/2014 | Yen et al. | |
| 2016/0013427 A1* | 1/2016 | Kim | H01L 51/0074 |
| | | | 257/40 |

* cited by examiner

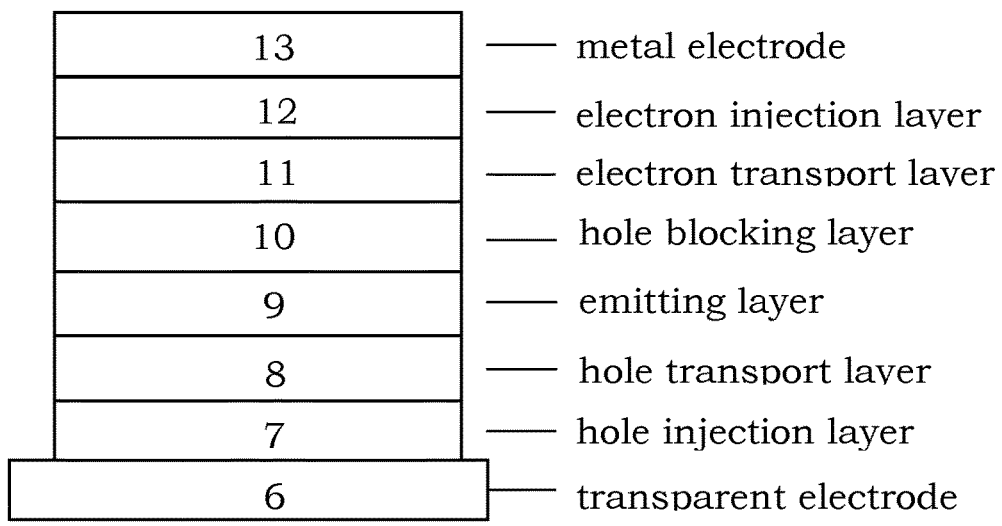

ORGANIC MATERIAL AND ORGANIC ELECTROLUMINESCENT DEVICE USING THE SAME

This application is a Continuation-in-Part of U.S. Pat. Ser. No. 14/585,219, filed Dec. 30, 2014.

FIELD OF INVENTION

The present invention generally relates to an organic material containing indenotriphenylene derivatives and organic electroluminescent (herein referred to as organic EL) device using the organic material. More specifically, the present invention relates to an organic material having general formula (I), an organic EL device employing the organic material as hole blocking layer (HBL), electron transport layer (ETL) and/or phosphorescent host can efficiently lower driving voltage, lower power consumption and increase the efficiency.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL is composed of layers of organic materials situated between two electrodes, which include a hole transporting layer (HTL), an emitting layer (EML), an electron transporting layer (ETL). The basic mechanism of organic electroluminescence involves the injection of the carrier, transport, recombination of carriers and exciton formed to emit light. When an external voltage is applied to an organic light-emitting device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic light-emitting diodes make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The phosphorescent organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, lower power consumption, the good thermal and electrochemical stability of the materials are also needed.

There continues to be a need for organic EL materials which is able to efficiently transport electrons and block holes, with lower power consumption, good thermal stability and high emitting efficiency. According to the reasons described above, the present invention has the objective of resolving such problems of the prior-art and offering an organic EL device which is excellent in its lower power consumption, thermal stability, high luminance and long half-life time. The present invention disclose a novel organic material containing indenotriphenylene derivatives having general formula (I), used as hole blocking layer (HBL), electron transport layer (ETL) and/or phosphorescent host have good charge carrier mobility and excellent operational durability can efficiently lower driving voltage and power consumption, increasing efficiency of organic EL device.

SUMMARY OF THE INVENTION

In accordance with the present invention, the organic material for hole blocking material (herein referred to as HBM), electron transport material (herein referred to as ETM) and/or phosphorescent host and their use for organic EL device are provided. The organic material can overcome the drawbacks of the conventional materials like as lower efficiency and higher power consumption.

An object of the present invention is to provide the organic material which can be used as hole blocking material (HBM), hole blocking electron transport material (HBETM) for organic EL device and can efficiently confine excitons to transfer to electron transport layer.

An object of the present invention is to provide the organic material which can be used as electron transport material (ETM) for organic EL device.

An object of the present invention is to provide the organic material which can be used as phosphorescent host material of emitting layer for organic EL device.

Another object of the present invention is to apply the organic material for organic EL device and lower driving voltage, lower power consumption and increase the efficiency.

The present invention has the economic advantages for industrial practice. Accordingly the present invention, the organic material which can be used for organic EL device is disclosed. The mentioned the organic material is represented by the following formula (I):

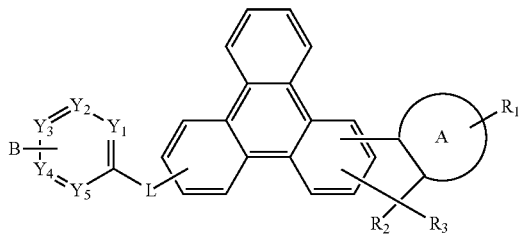

formula(I)

wherein A ring represents a phenyl group and fused ring hydrocarbon units with two to four rings group, L represents a single bond, a substituted or unsubstituted divalent arylene group having 6 to 30 ring carbon atoms or a substituted or unsubstituted divalent heteroarylene group having 6 to 30 ring carbon atoms, $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms, $Y_1$ to $Y_5$ each independently represent nitrogen atom or $CR_5$, $R_5$ independently represent a hydrogen atom, a substituted or unsubstituted phenylene group having 6 to 30 ring carbon atoms, or a bond linked to B; B stand for a group of following formula (II):

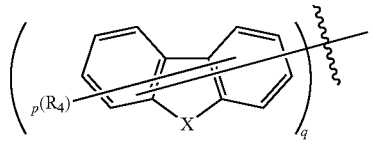

formula(II)

wherein q represents an integer of 0 to 3, p represents an integer of 0 to 7, X represents O, S, $NR_6$, $R_6$ independently represents a hydrogen atom, a substituted or unsubstituted phenyl group, a substituted or unsubstituted carbazole group, and a bond linked to formula (I), $R_4$ is the same definition as $R_1$.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transporting layer which is deposited onto 7, 9 is fluorescent or phosphorescent emitting layer which is deposited onto 8, 10 is hole blocking layer which is deposited onto 9, 11 is electron transporting layer which is deposited onto 10, 12 is electron injection layer which is deposited on to 11.

DESCRIPTION OF THE PREFERRED EMBODIMENTS

What probed into the invention is the organic material and organic EL device using the organic material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic material which can be used as hole blocking material (herein referred to as HBM), electron transport material (herein referred to as ETM) and/or phosphorescent host for organic EL device are disclosed. The mentioned organic material are represented by the following formula (I)

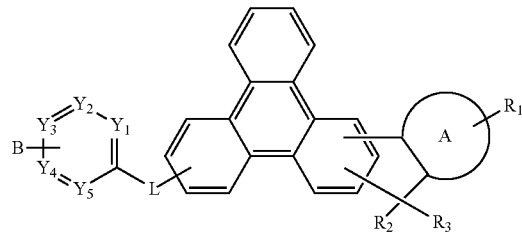

formula(I)

wherein A ring represents a phenyl group and fused ring hydrocarbon units with two to four rings group, L represents a single bond, a substituted or unsubstituted divalent arylene group having 6 to 30 ring carbon atoms or a substituted or unsubstituted divalent heteroarylene group having 6 to 30 ring carbon atoms, $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms, $Y_1$ to $Y_5$ each independently represent nitrogen atom or $CR_5$, $R_5$ independently represent a hydrogen atom, a substituted or unsubstituted phenylene group having 6 to 30 ring carbon atoms, or a bond linked to B; B stand for a group of following formula (II):

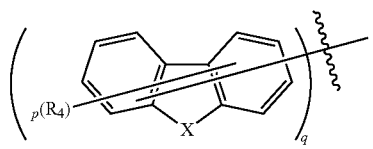

formula(II)

wherein q represents an integer of 0 to 3, p represents an integer of 0 to 7, X represents O, S, $NR_6$, $R_6$ independently represents a hydrogen atom, a substituted or unsubstituted phenyl group, a substituted or unsubstituted carbazole group, and a bond linked to formula (I), $R_4$ is the same definition as $R_1$.

According to the above-mentioned formula (I) wherein L is represented the following formulas:

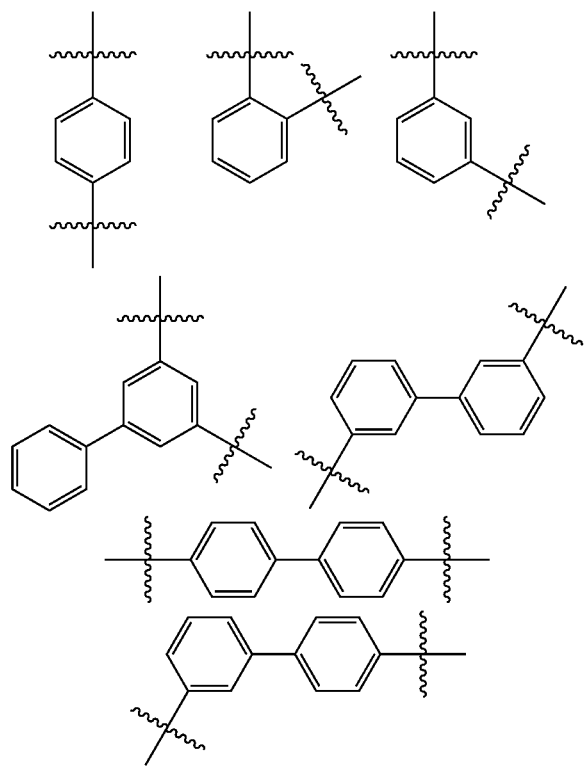

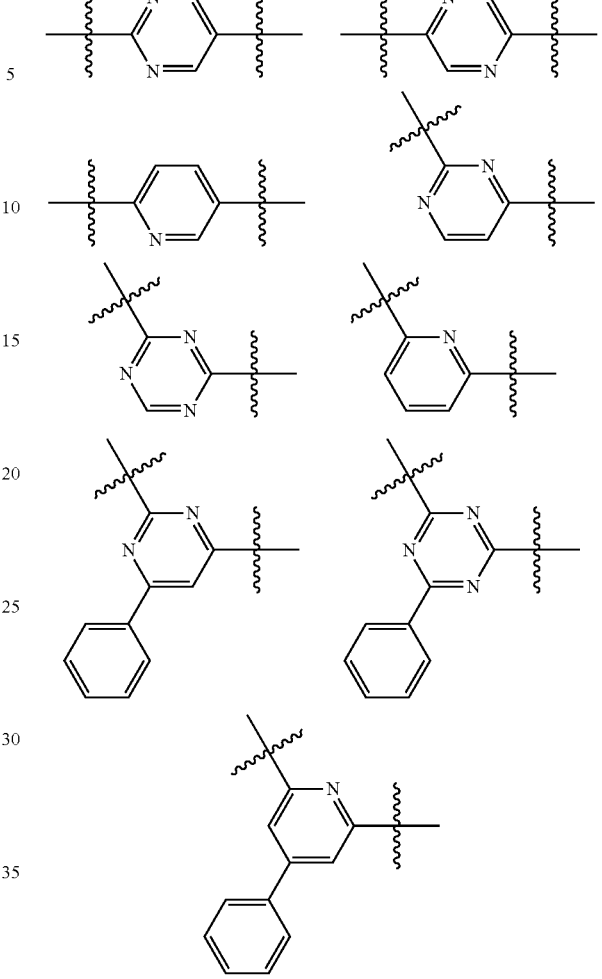

According to the above-mentioned formula (I) wherein A ring represents a phenyl group and fused ring hydrocarbon units with two to four rings group including naphthyl group, anthracenyl group, phenanthrenyl group, pyrenyl group, chrysenyl group and triphenylene group.

In this embodiment, some organic materials according formula (I) are shown below:

EX1

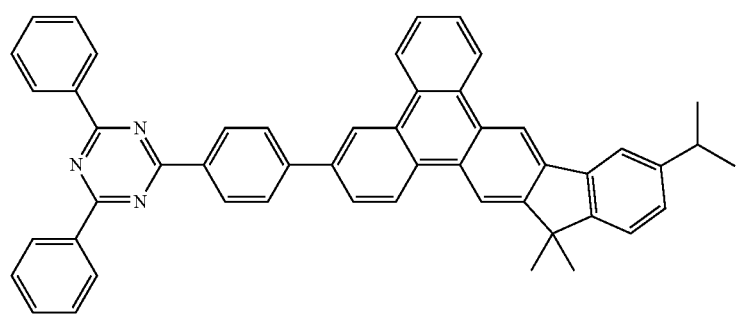

-continued
EX2
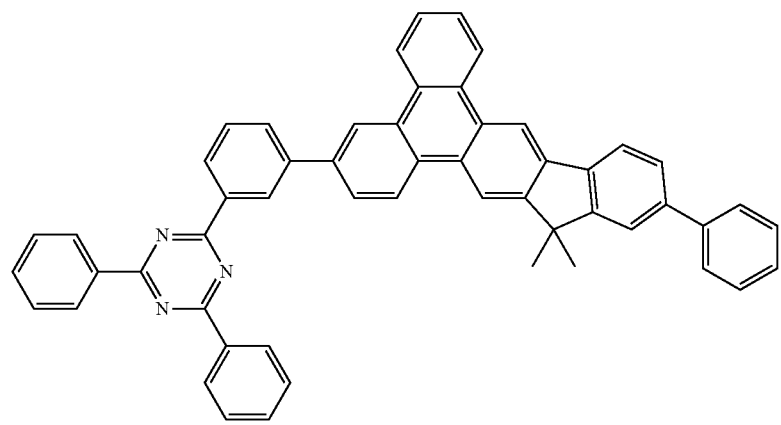
EX3
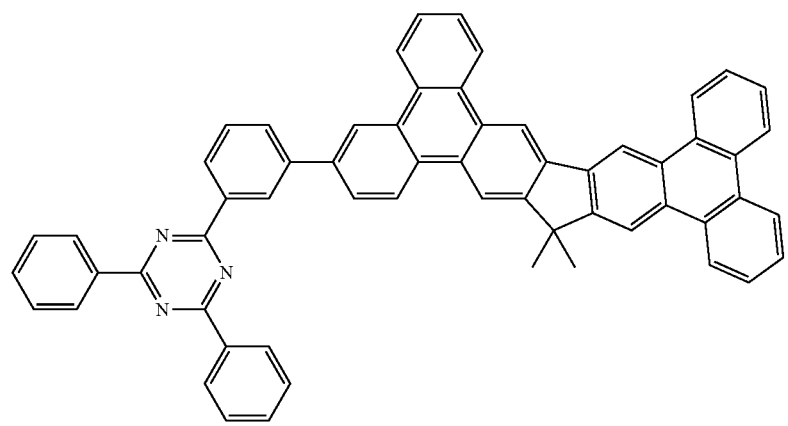
EX4
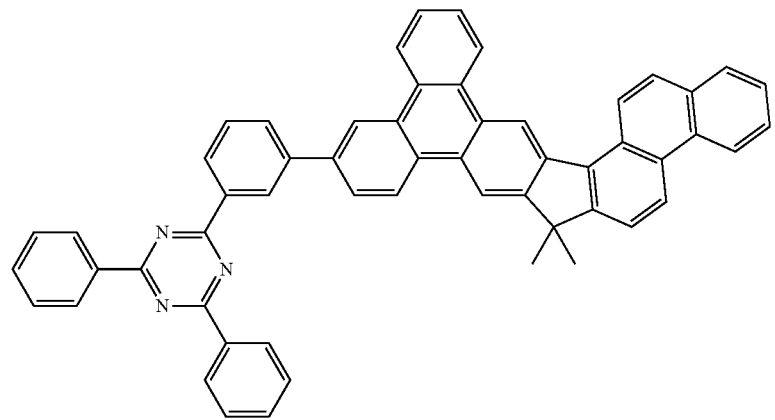
EX5
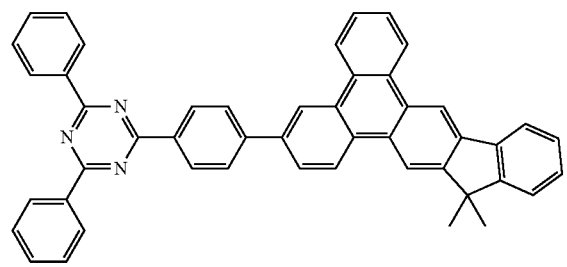
EX6
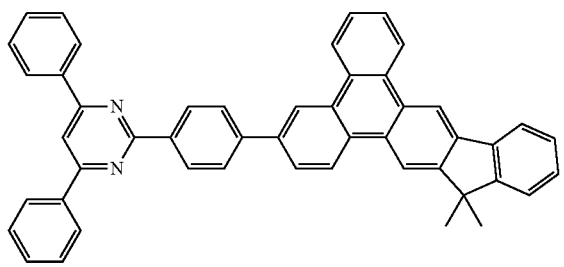

-continued
EX7
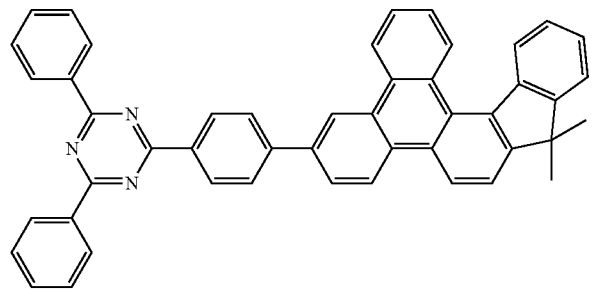
EX8
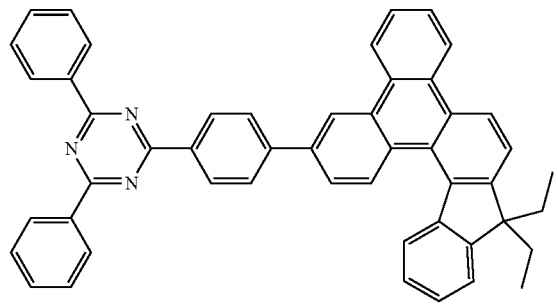
EX9
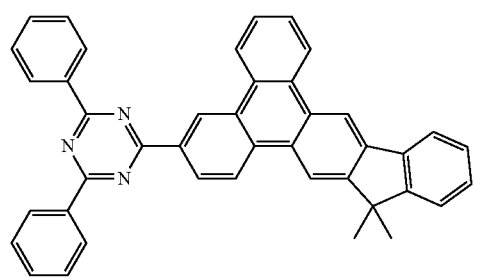
EX10
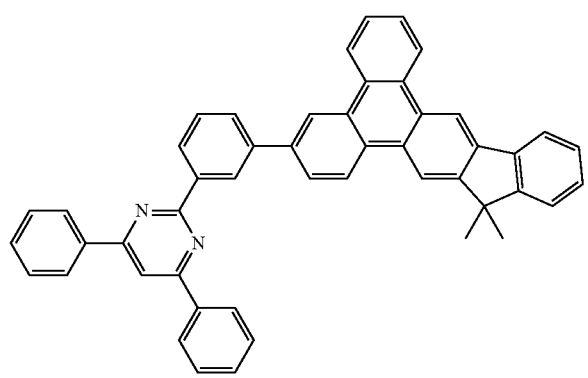
EX11
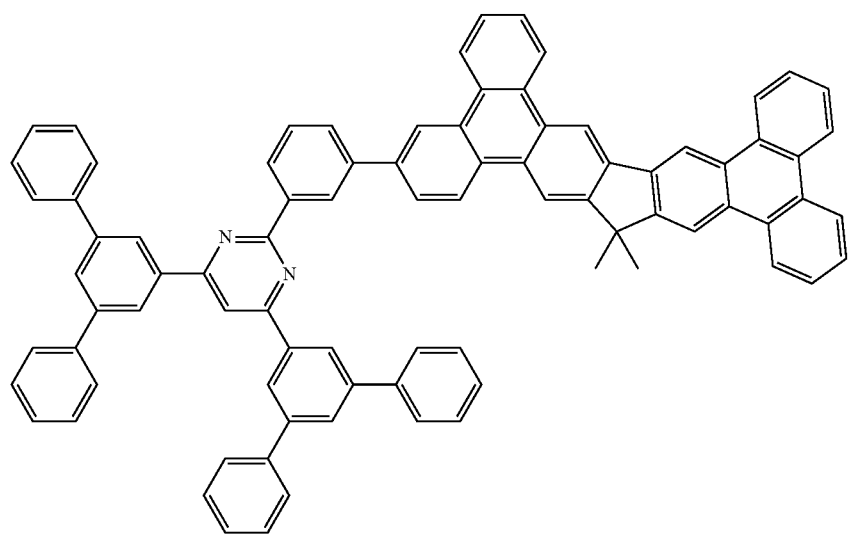

EX12
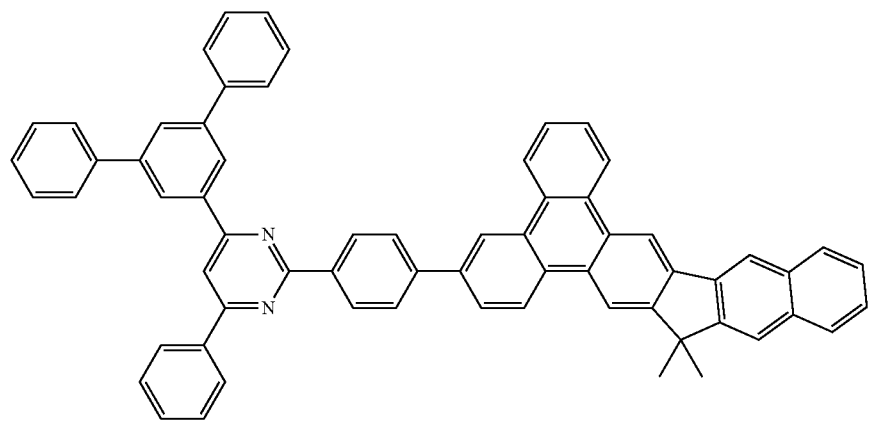
EX13 EX14
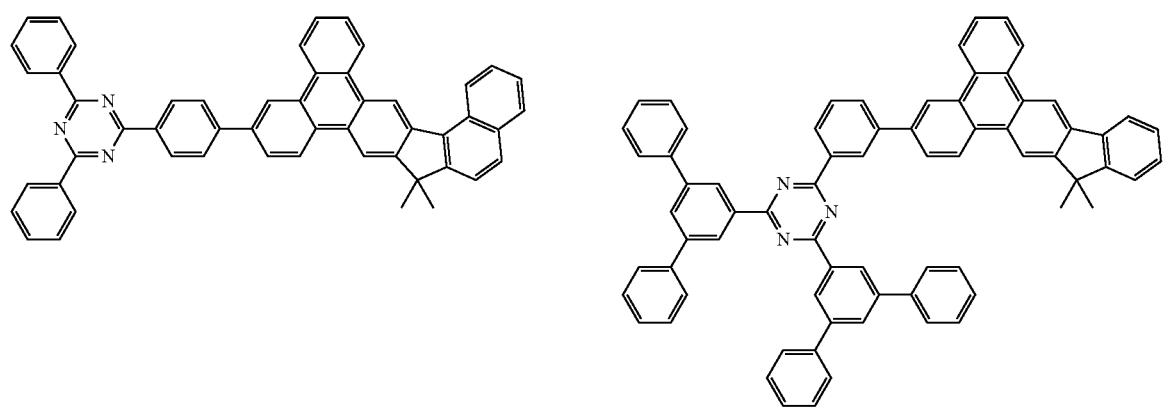
EX15
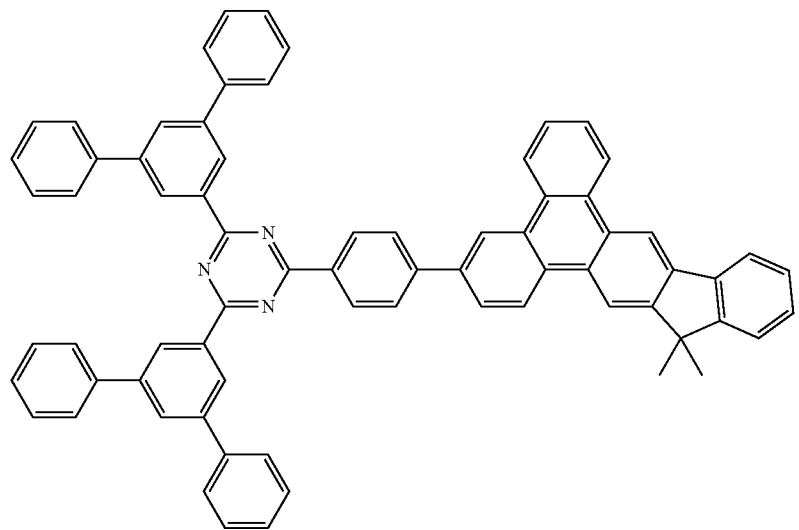

-continued
EX16
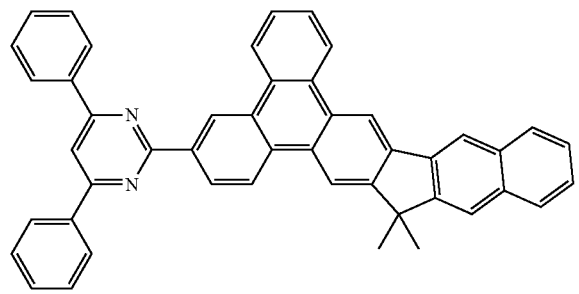
EX17
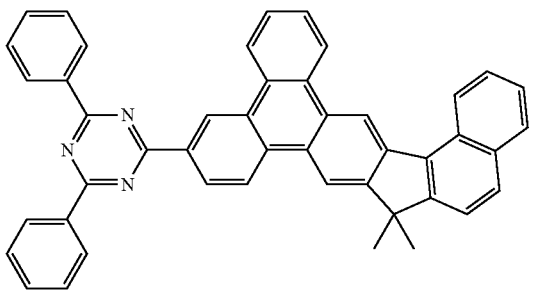
EX18
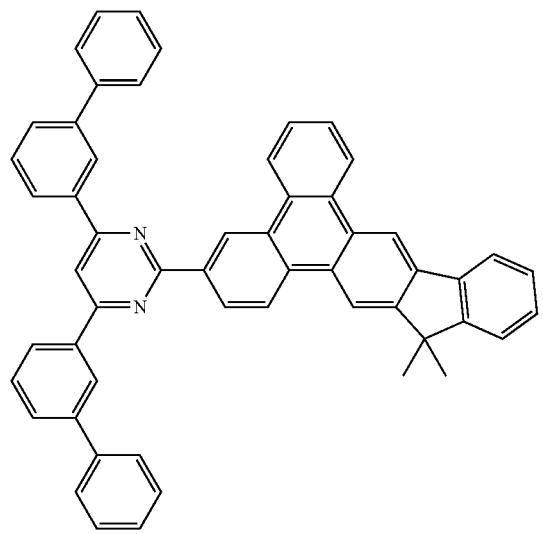
EX19
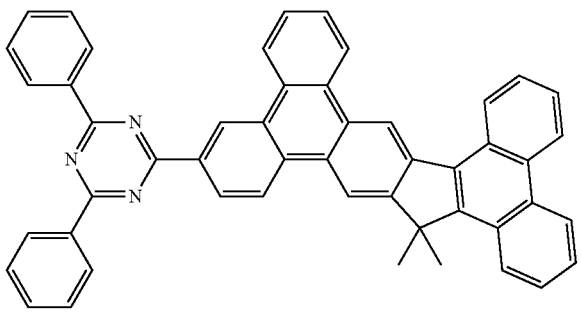
EX20
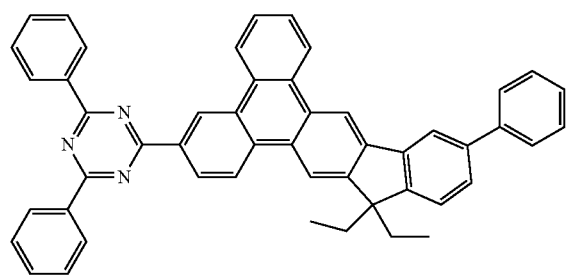
EX21
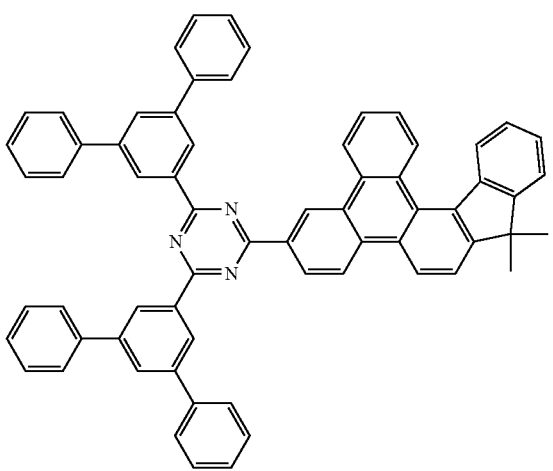

EX22
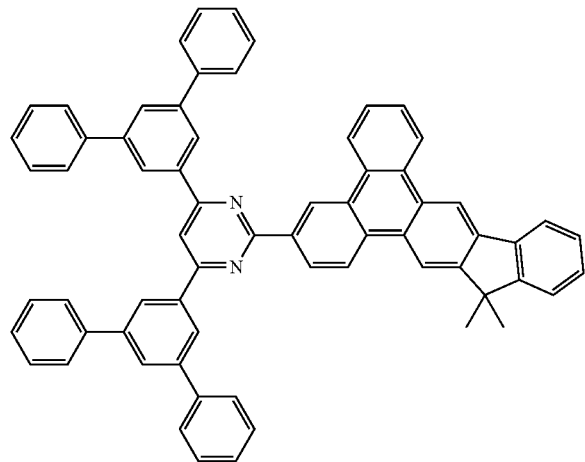
EX23
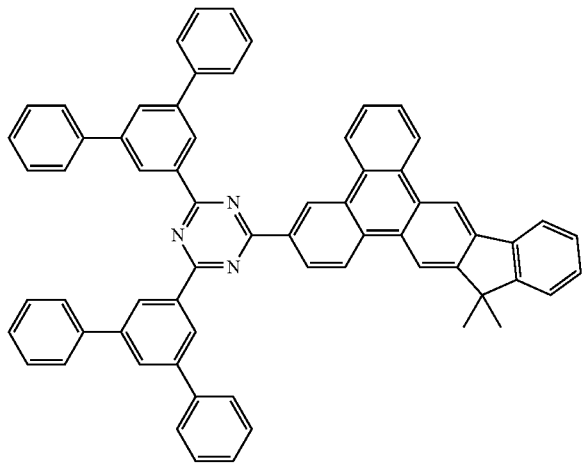
EX24
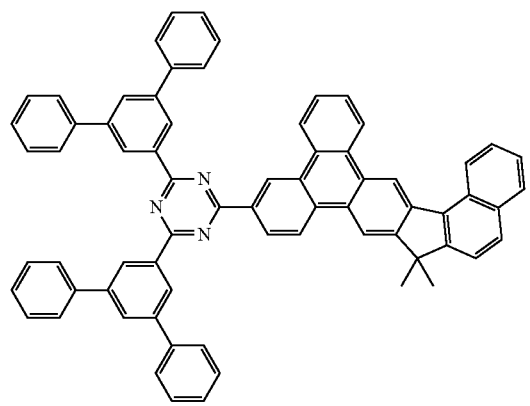
EX25
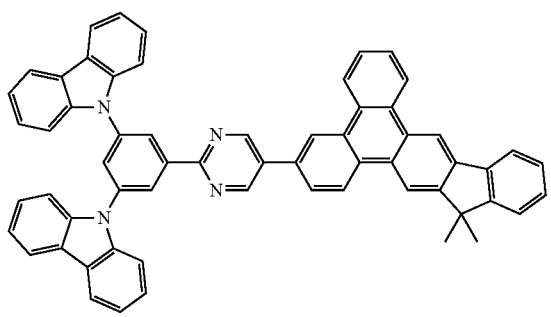
EX26
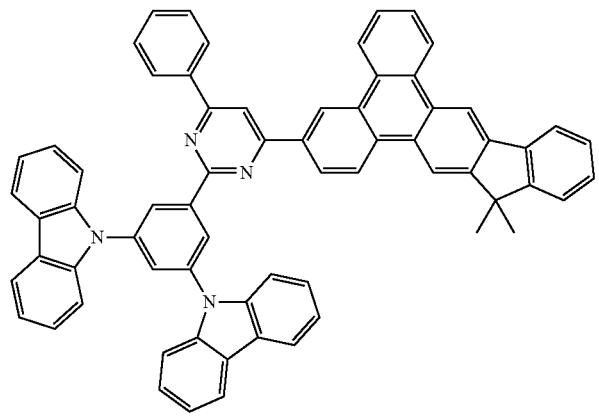
EX27
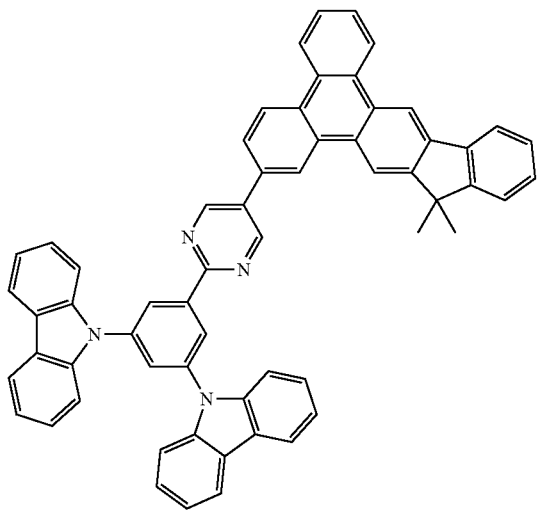

-continued
EX28
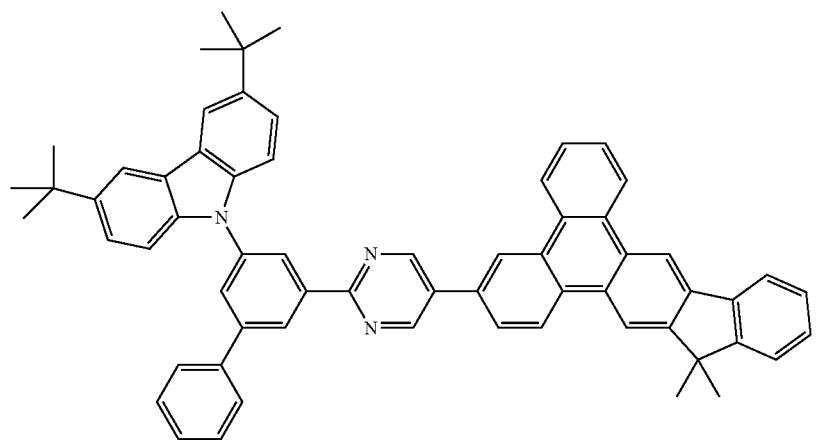
EX29
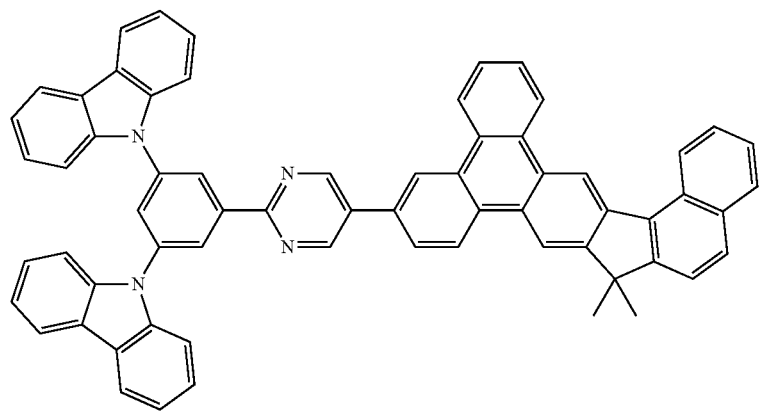
EX30
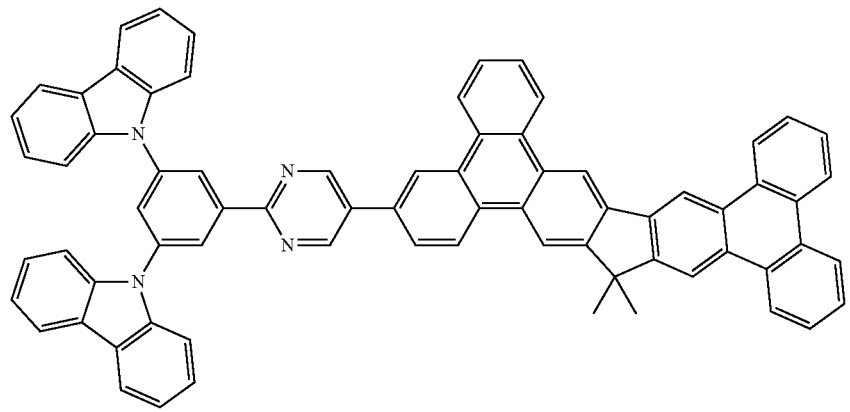
EX31
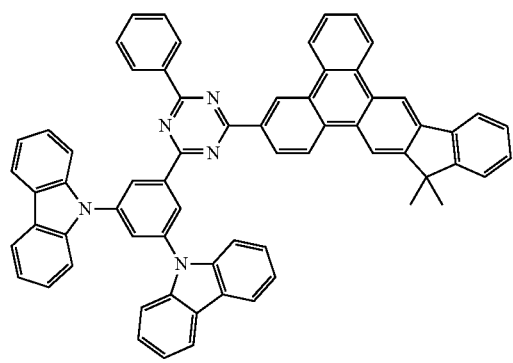
EX32
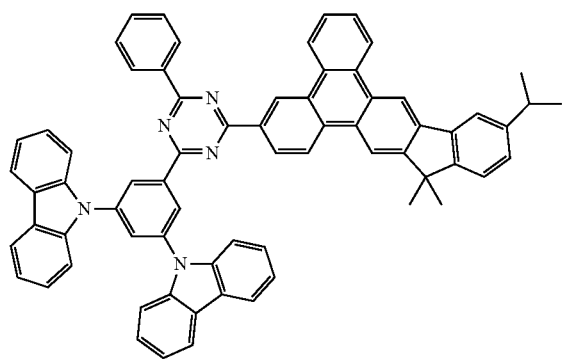

EX33
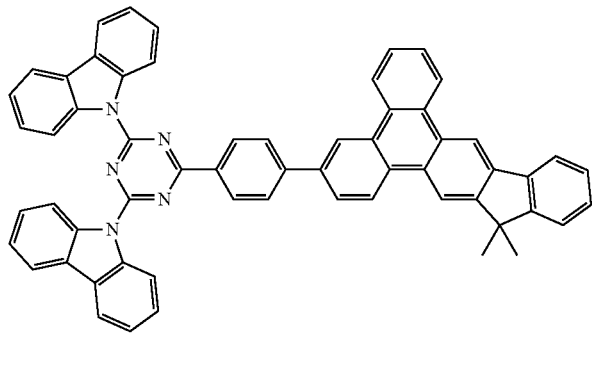
EX34
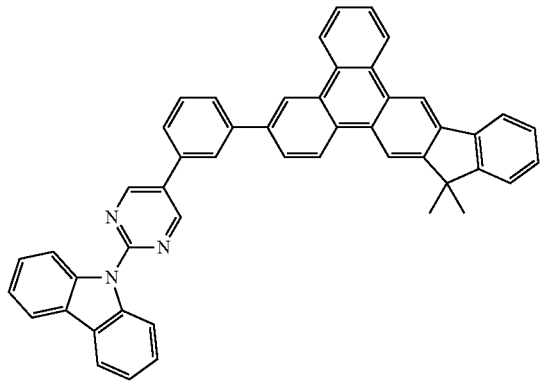
EX35
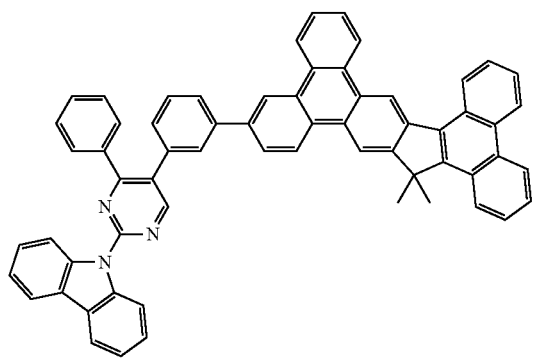
EX36
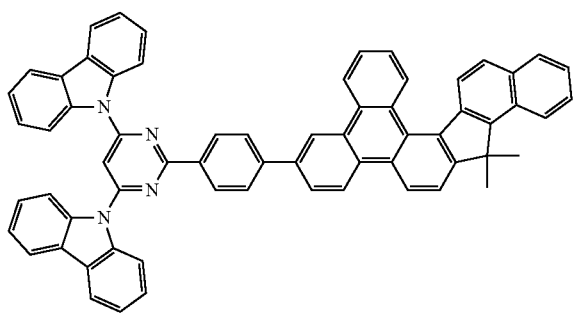
EX37
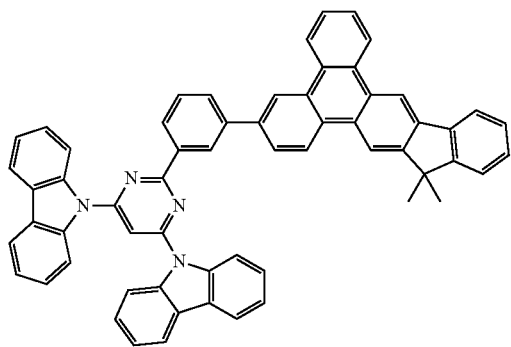
EX38
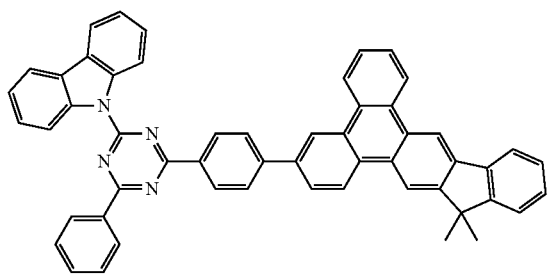
EX39
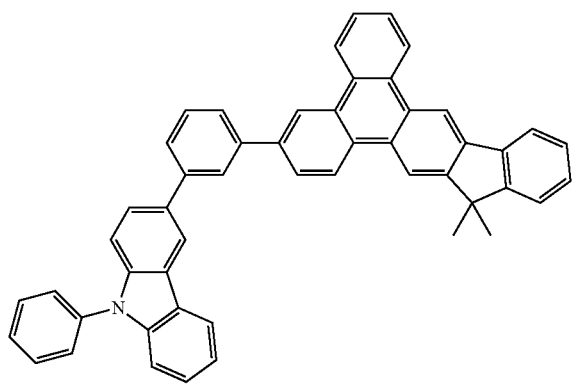
EX40
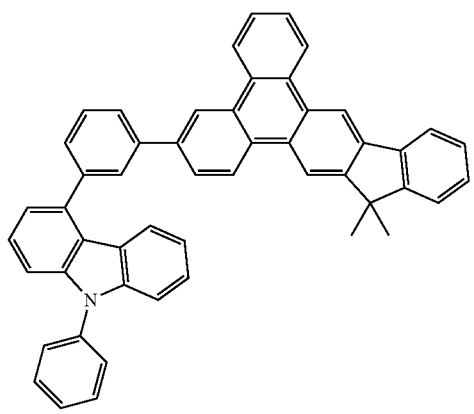

-continued
EX41
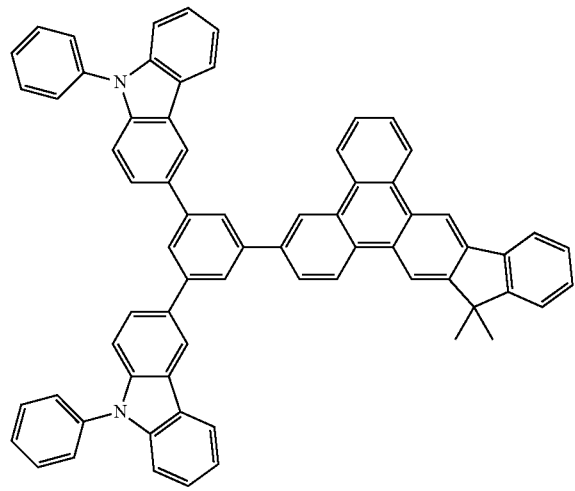
EX42
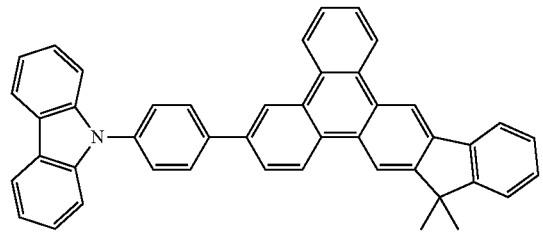
EX43
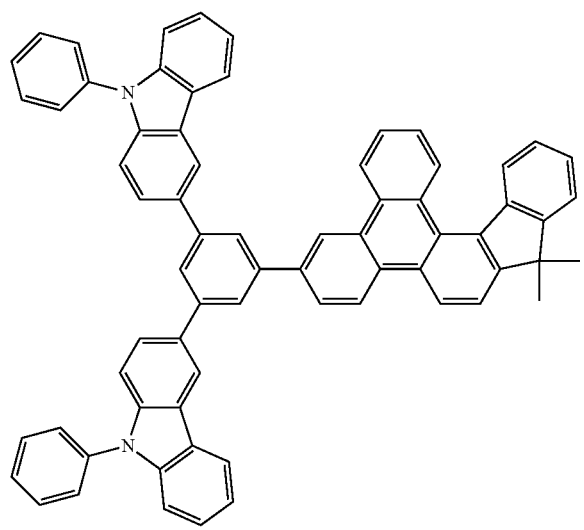
EX44
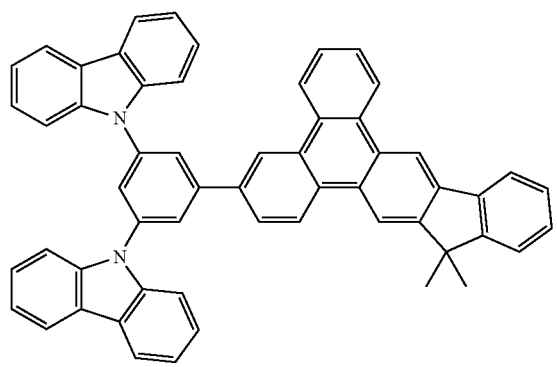
EX45
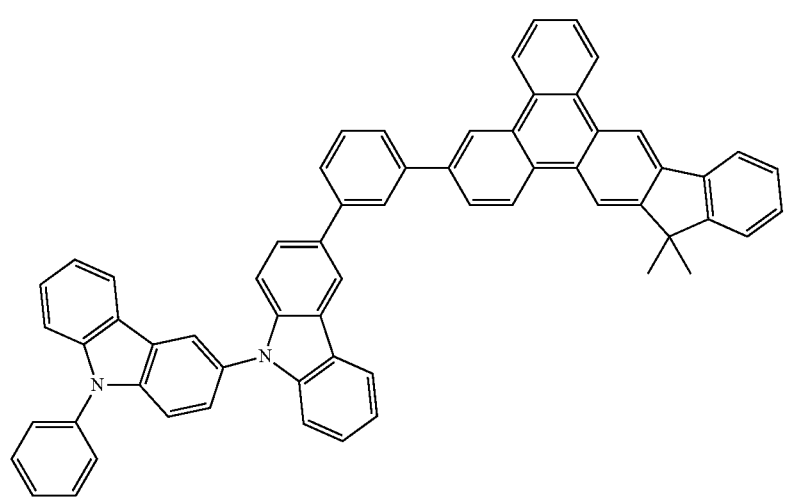

-continued
EX46
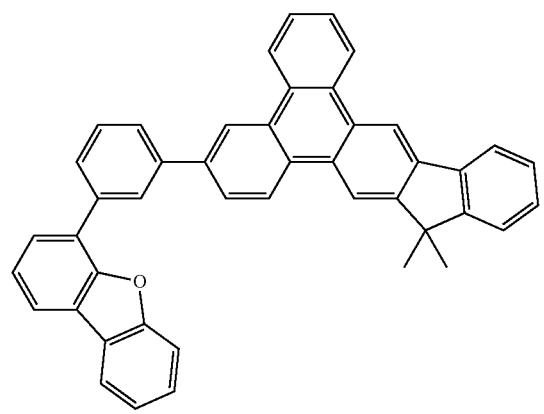
EX47
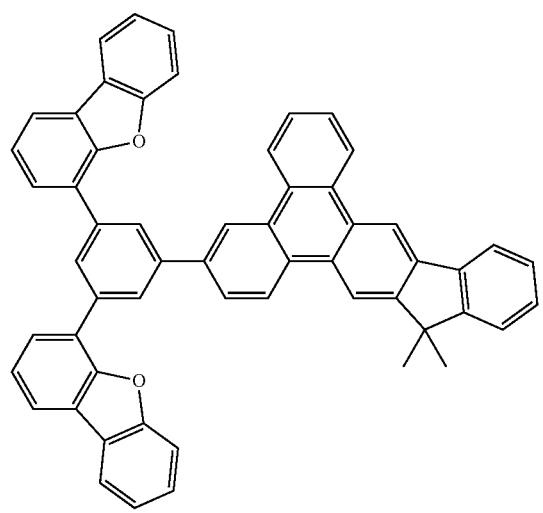
EX48
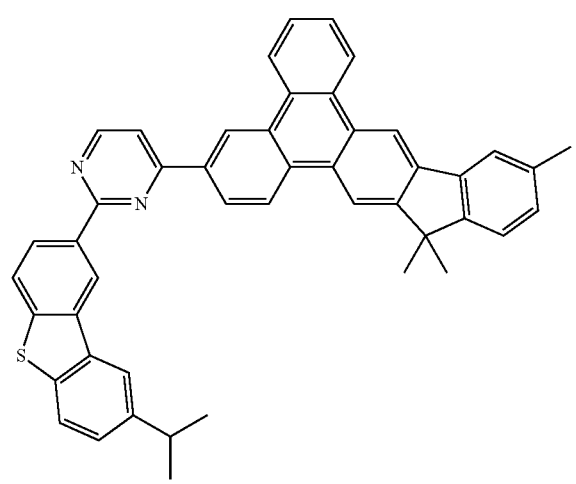
EX49
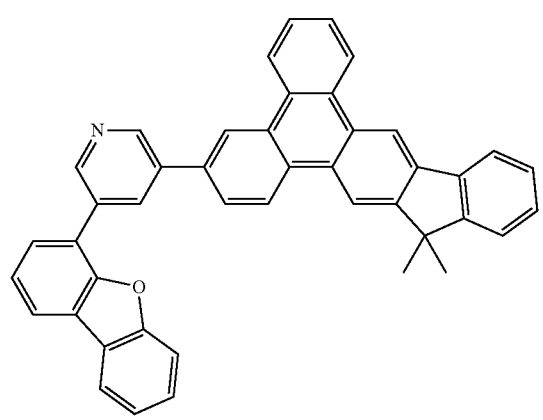
EX50
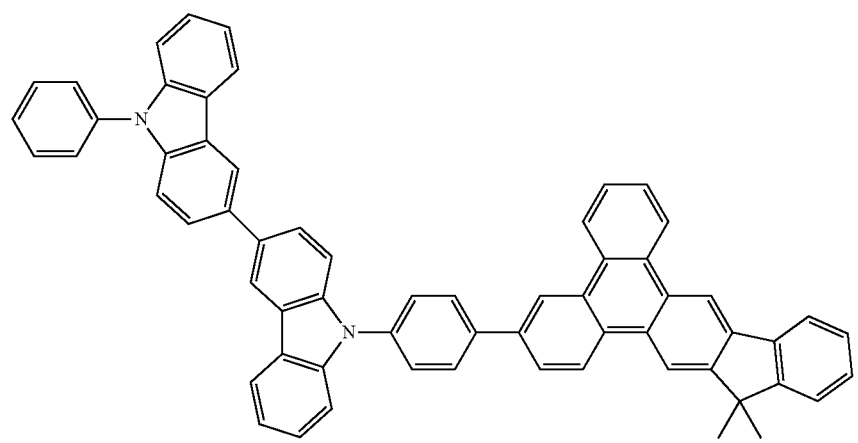

-continued
EX51
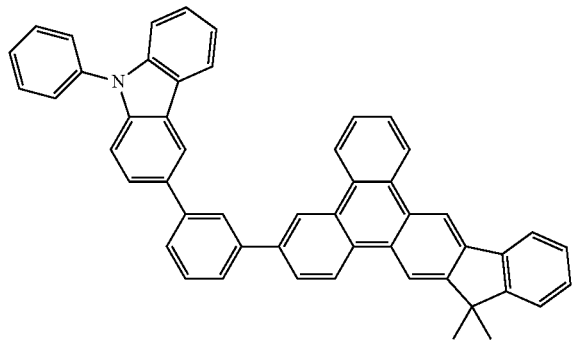
EX52
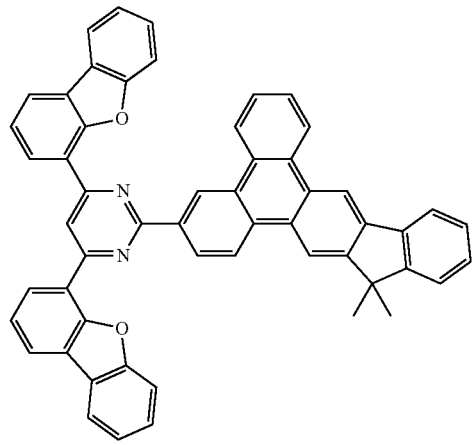
EX53
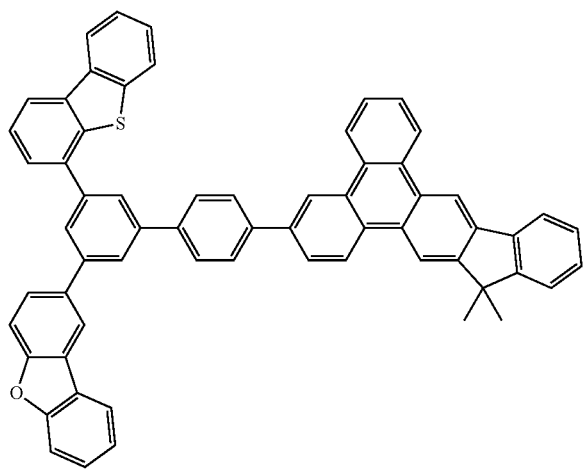
EX54
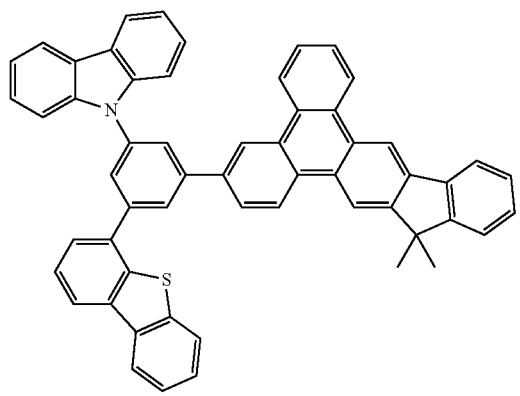
EX55
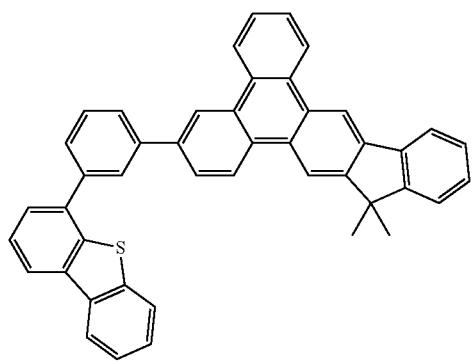
EX56
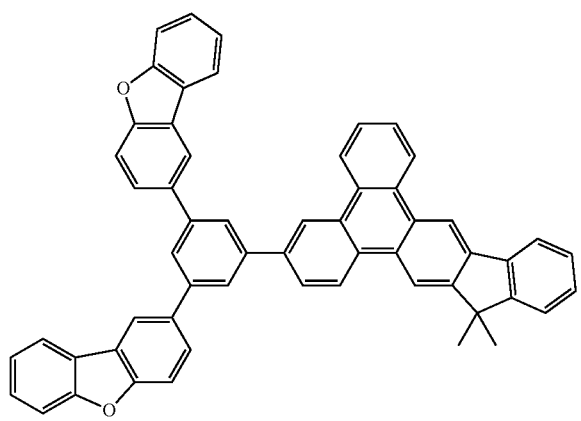

-continued
EX57
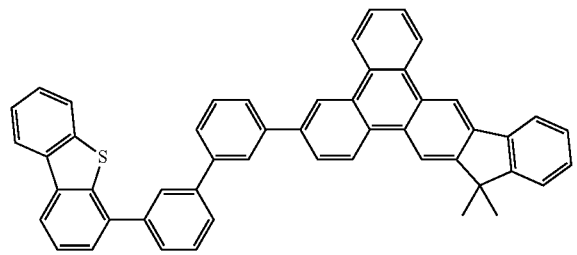
EX58
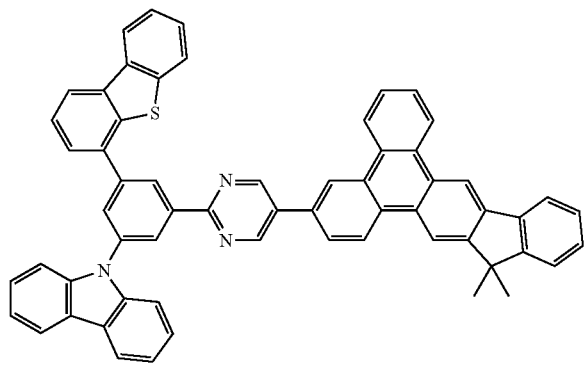
EX59
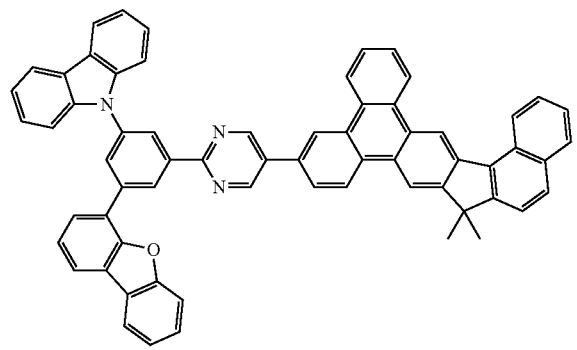
EX60
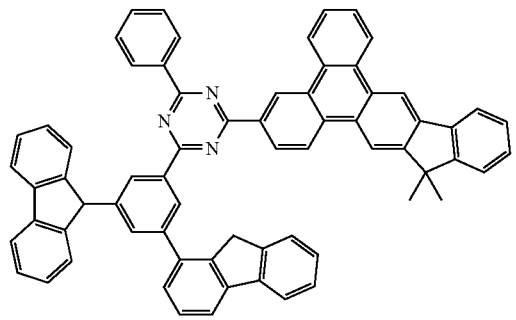
EX61
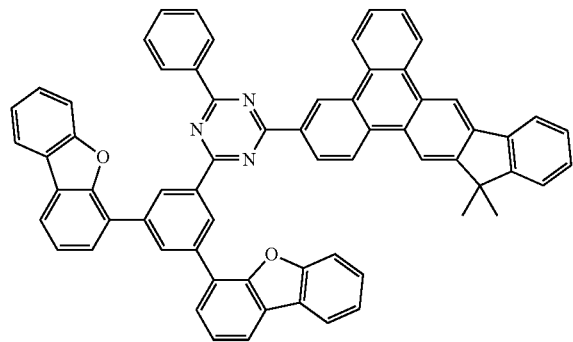
EX62
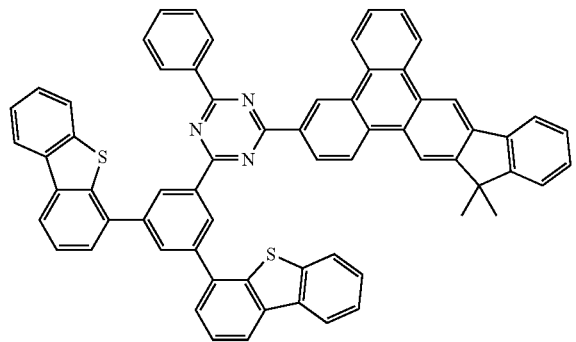

Detailed preparation for the organic material in the present invention could be clarified by exemplary embodiments, but the present invention is not limited to exemplary embodiments. EXAMPLE 1~14 show the preparation for some EXAMPLES of the organic material in the present invention. EXAMPLE 15 and 16 show the fabrication of organic EL device and I-V-B, half-life time of organic EL device testing report.

Example 1

Synthesis of EX5

Synthesis of 2-bromo-5-nitrobiphenyl

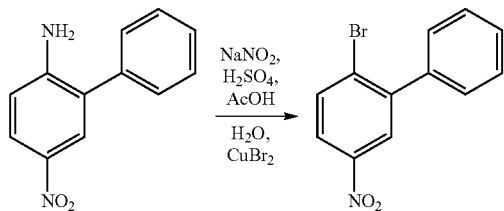

2.6 g (12.14 mmol) of 2-phenyl-4-nitroaniline was added to a mixture of 0.92 g (13.35 mmol) of sodium nitrite, 8 ml of sulfuric acid, 9 ml of acetic acid at 0-5° C. and stirred for 2 hr at 0-5° C. Water was added to this mixture and stirred for 1 hr at room temperature. 4.3 g (19.42 mmol) of copper(II) bromide dissolved in 9.3 ml 2M HCl solution was added and stirred for 20 min at room temperature, then heated to 60° C. for 1 hr. After finishing the reaction, the organic layer was extracted with ether and water, washed with brine, dried over magnesium sulfate and evaporated to dryness and the crude was purified by column chromatography on silica to give product (1.5 g, 5.39 mmol, 45.5%) as a white solid.

Synthesis of 9,9-dimethyl-2-(5-nitrobiphenyl-2-yl)-9H-fluorene

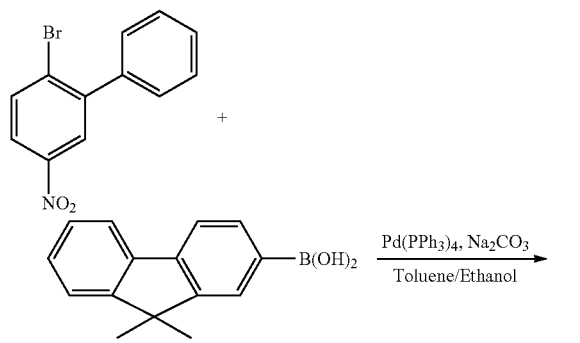

A mixture of 40 g (14.38 mmol) of 2-bromo-5-nitrobiphenyl, 27.7 g (15.82 mmol) of 9,9-dimethyl-9H-fluoren-2-ylboronic acid, 1.8 g (0.16 mmol) of Pd(PPh$_3$)$_4$, 119 ml of 2M Na$_2$CO$_3$, 150 ml of EtOH and 450 ml toluene was degassed and placed under nitrogen, and then heated at 100° C. overnight. After finishing the reaction, the mixture was allowed to cool to room temperature. The solution was extracted with dichloromethane and water. The organic layer was dried with anhydrous magnesium sulfate and the solvent was evaporated under reduced pressure. The residue was purified by column chromatography on silica to give product 43.1 g(110.1 mmol, 69.6%).1H NMR (CDCl3, 400 MHz): chemical shift (ppm) 7.93(s, 1H), 7.71(d, 1H), 7.50(d, 1H), 7.38~7.21(m, 6H), 7.16~6.92(m, 4H), 6.83~6.65(m, 2H), 1.15(s, 6H)

Synthesis of 6-(9,9-dimethyl-9H-fluoren-2-yl)biphenyl-3-amine

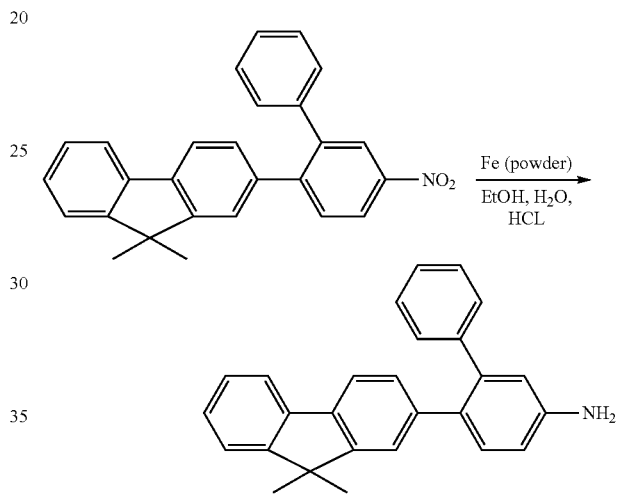

A mixture of 10.4 g (26.56 mmol) of 9,9-dimethyl-2-(5-nitrobiphenyl-2-yl)-9H-fluorene, 8.5 g (159.36 mmol) of iron powder and 10 ml of conc. HCl was refluxed in aqueous ethanol (100 mL of alcohol and 30 mL of water) at 85° C. for 2 h. The reaction mixture was filtered and the filtrate was extracted with ethyl acetate and water. The organic layer was dried with anhydrous magnesium sulfate and the solvent was evaporated under reduced pressure. Formed solid was washed with hexane to yield product 8.2 g(22.68 mmol, 85%).1H NMR(CDCl3, 400 MHz): chemical shift(ppm) 7.71(d, 1H), 7.64(d, 1H), 7.42(d, 1H), 7.29~7.12(m, 7H), 7.06(d, 2H), 6.89(s, 1H), 6.80(d, 1H), 6.78(s, 1H), 4.47(s, 2H), 1.12(s, 6H).

Synthesis of 2-(5-bromobiphenyl-2-yl)-9,9-dimethyl-9H-fluorene

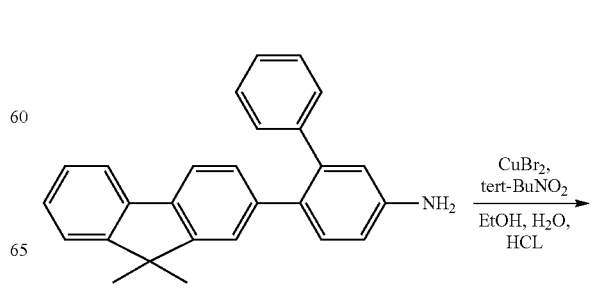

-continued

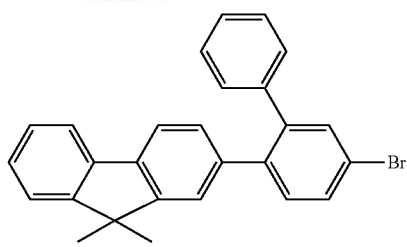

To a refluxing mixture of 0.34 g (3.32 mmol) of tert-butyl nitrite, 0.6 g (2.76 mmol) of anhydrous copper(II) bromide and anhydrous acetonitrile (46 mL), 1 g (2.76 mmol) of the corresponding 6-(9,9-dimethyl-9H-fluoren-2-yl)-biphenyl-3-amine was added slowly over a period of 1 h giving rise to a reaction with vigorous foaming and evolution of nitrogen gas. After completion of the reaction, the mixture was cooled to room temperature and poured into an aqueous HCl solution. The crude which precipitated was purified by column chromatography on silica to give product 0.3 g(0.70 mmol, 25%).1H NMR(CDCl3, 400 MHz): chemical shift (ppm) 7.81(d, 1H), 7.68~7.66(m, 1H), 7.63~7.61(m, 1H), 7.37~7.35(m, 1H), 7.32~7.24(m, 4H), 7.22~7.16(m, 4H), 7.12~7.09(m, 2H), 6.93(d, 1H), 1.20(s, 6H).

Synthesis of 6-bromo-10,10-dimethyl-10H-indeno[2,1-b]triphenylene

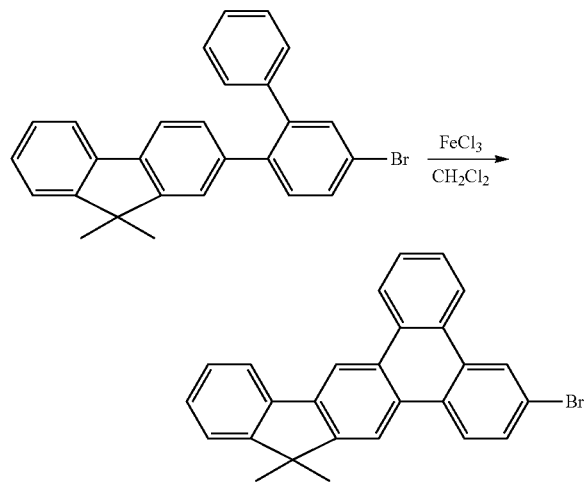

In a 100 ml three-necked flask that had been degassed and filled with nitrogen, 2.9 g (0.68 mmol) of 2-(5-bromobiphenyl-2-yl)-9,9-dimethyl-9H-fluorene was dissolved in anhydrous dichloromethane (180 ml), 5.5 g (3.40 mmol) of iron(III) chloride was then added, and the mixture was stirred one hour. The reaction was quenched with methanol and water and the organic layer was separated and the solvent was removed. The residue was purified by column chromatography on silica afforded a white solid (1.7 g, 0.81 mmol, 58.6%).1H NMR(CDCl3, 400 MHz): chemical shift (ppm) 9.01(s, 1H), 8.94(d, 2H), 8.78(s, 1H), 8.58(s, 1H), 8.49(s, 1H), 7.98(d, 1H), 7.85~7.78(m, 2H), 7.63~7.43(m, 4H), 1.69(s, 6H).

Synthesis of 2-(10,10-dimethyl-10H-indeno[2,1-b]triphenylen-6-yl)-4,4,5,5-tetramethyl-1,3,2-dioxaborolane

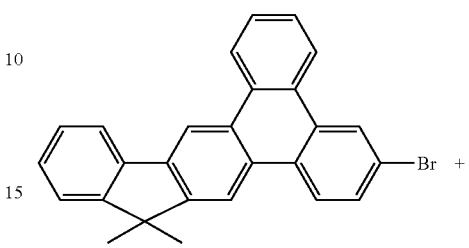

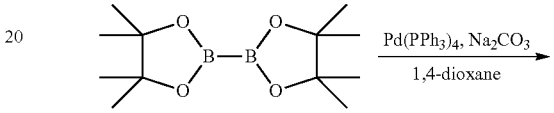

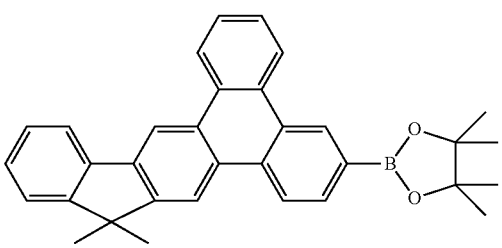

A mixture of 3 g (7 mmol) of 6-bromo-10,10-dimethyl-10H-indeno[2,1-b]triphenylene, 2.16 g (8.4 mmol) of 4,4,4',4',5,5,5',5'-octamethyl-2,2'-bi(1,3,2-dioxaborolane), 0.16 g (0.14 mmol) of Pd(PPh3)4, 50 ml 1,4-dioxane was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (2.27 g, 4.8 mmol, 69%) as a white solid.

Synthesis of 2-(4-(10,10-dimethyl-10H-indeno[2,1-b]triphenylen-6-yl)phenyl)-4,6-diphenyl-1,3,5-triazine (EX5)

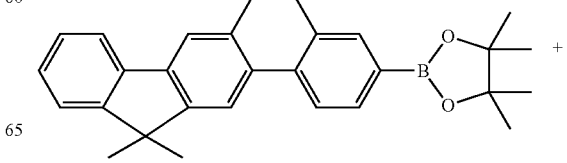

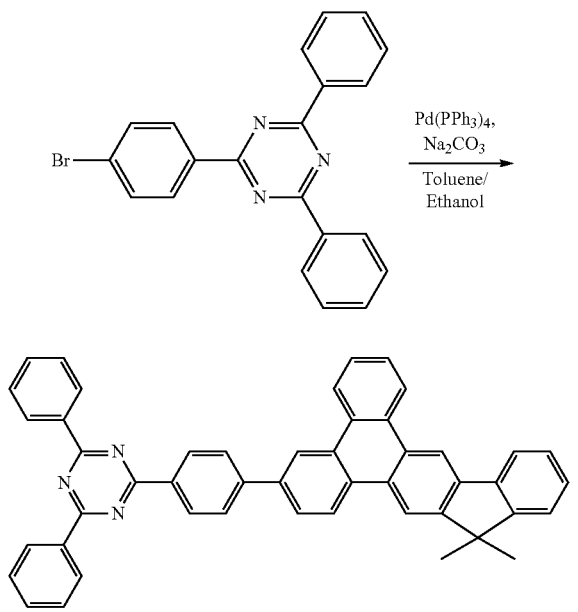

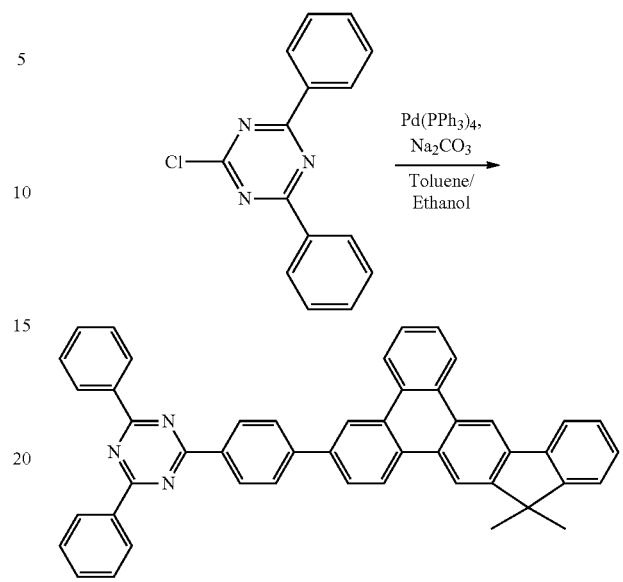

A mixture of 3 g (6.38 mmol) of 2-(10,10-dimethyl-10H-indeno[2,1-b]triphenylen-6-yl)-4,4,5,5-tetramethyl-1,3,2-dioxaborolane, 1.90 g (4.90 mmol) of 2-(4-bromophenyl)-4,6-diphenyl-1,3,5-triazine, 0.05 g (0.05 mmol) of Pd(PPh$_3$)$_4$, 9.8 ml of 2M Na$_2$CO$_3$, 15 ml of EtOH and 45 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (1.75 g, 2.67 mmol, 55%) as a pale yellow solid. 1H NMR(CDCl3, 400 MHz): chemical shift(ppm) 9.03(s, 1H), 8.97~8.77(m, 3H), 8.58(s, 1H), 8.49~8.31(m, 7H), 7.98(d, 1H), 7.85~7.78(m, 2H), 7.63~7.43(m, 12H), 1.69(s, 6H). MS(m/z, FAB$^+$):651.5

2-chloro-4,6-diphenyl-1,3,5-triazine instead of 2-(4-bromo phenyl)-4,6-diphenyl-1,3,5-triazine, except for using the same method as in synthesis Example 1, the desired compound of 2-(10,10-dimethyl-10H-indeno[2,1-b]triphenylen-6-yl)-4,6-diphenyl-1,3,5-triazine(1.26 g, yield=45%) was obtained. MS(m/z, FAB$^+$):575.6

Example 3

Synthesis of EX10

Synthesis of 2-(3-(10,10-dimethyl-10H-indeno[2,1-b]triphenylen-6-yl)phenyl)-4,6-diphenylpyrimidine Example 2

Synthesis of EX9

Synthesis of 2-(10,10-dimethyl-10H-indeno[2,1-b]triphenylen-6-yl)-4,6-diphenyl-1,3,5-triazine

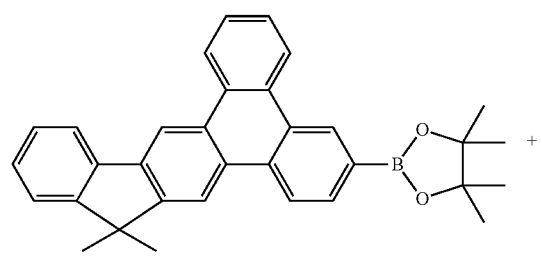

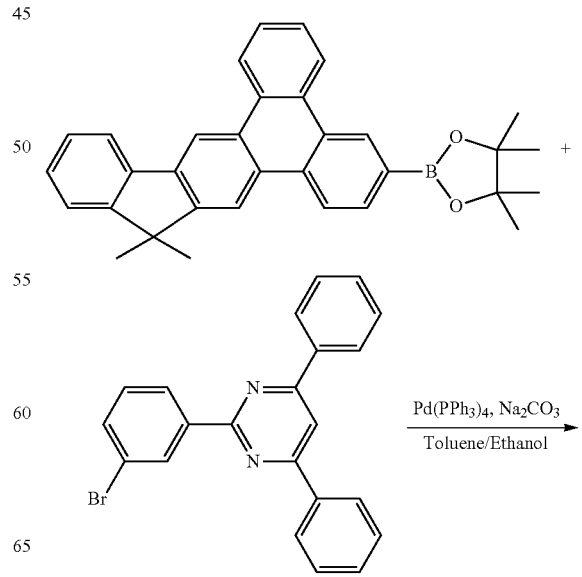

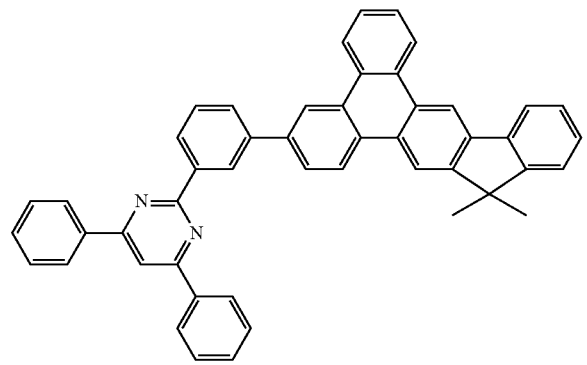

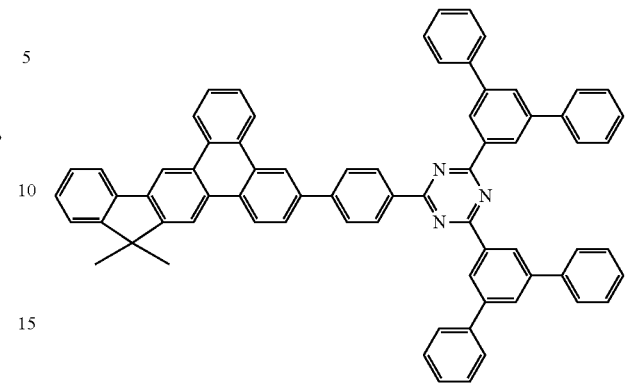

2-(3-bromophenyl)-4,6-diphenylpyrimidine instead of 2-(4-bromophenyl)-4,6-diphenyl-1,3,5-triazine, except for using the same method as in synthesis Example 1, the desired compound of 2-(3-(10,10-dimethyl-10H-indeno[2,1-b]triphenylen-6-yl)phenyl)-4,6-diphenylpyrimidine (3.08 g, yield=63%) was obtained. MS(m/z, FAB$^+$):650.8

Example 4

Synthesis of EX15

Synthesis of 2-(3-(10,10-dimethyl-10H-indeno[2,1-b]triphenylen-6-yl)phenyl)-4,6-bis([1,1':3',1''-terphenyl]-5'-yl)-1,3,5-triazine 2-(4-bromophenyl)-4,6-bis([1,1':3',1''-terphenyl]-5'-yl)-1,3,5-triazine instead of 2-(4-bromophenyl)-4,6-diphenyl-1,3,5-triazine, except for using the same method as in synthesis Example 1, the desired compound of 2-(3-(10,10-dimethyl-10H-indeno[2,1-b]triphenylen-6-yl)phenyl)-4,6-bis([1,1':3',1''-terphenyl]-5'-yl)-1,3,5-triazine (1.96 g, yield=42%) was obtained. MS (m/z, FAB$^+$):957.2

Example 5

Synthesis of EX33

Synthesis of 9,9'-(6-(4-(10,10-dimethyl-10H-indeno[2,1-b]triphenylen-6-yl)phenyl)-1,3,5-triazine-2,4-diyl)bis(9H-carbazole)

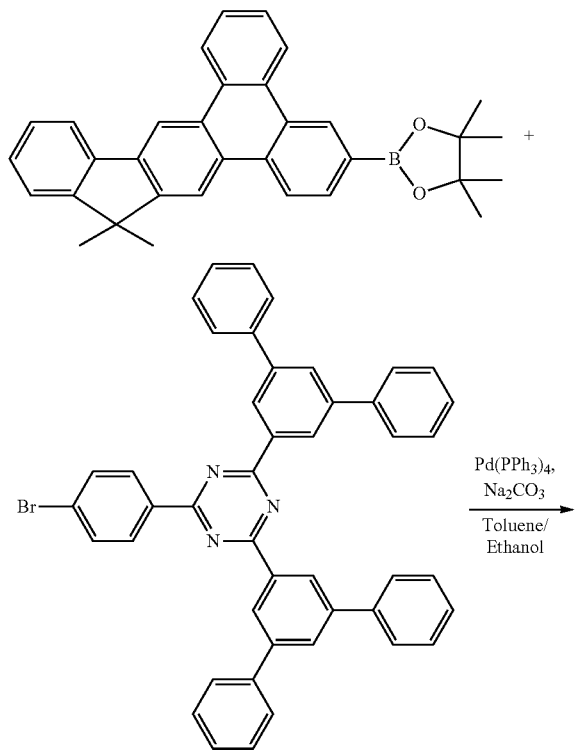

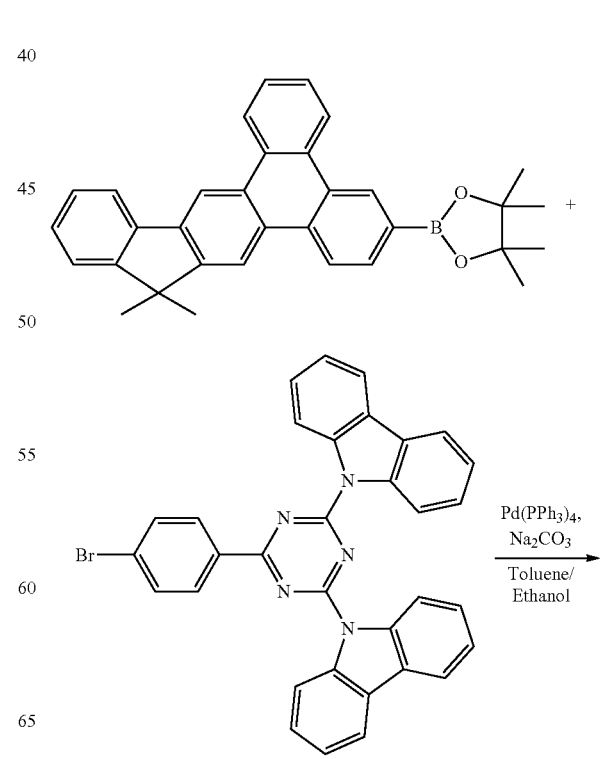

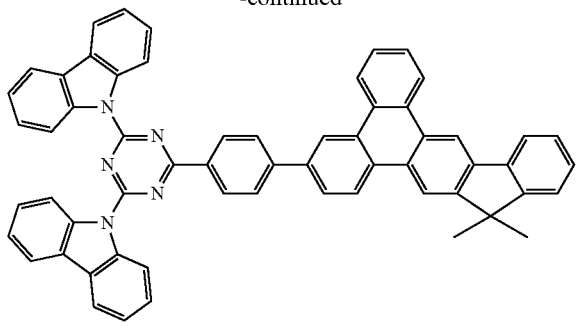

A mixture of 2 g (4.25 mmol) of 2-(10,10-dimethyl-10H-indeno[2,1-b]triphenylen-6-yl)-4,4,5,5-tetramethyl-1,3,2-dioxaborolane, 1.85 g (3.26 mmol) of 9,9'-(6-(4-bromophenyl)-1,3,5-triazine-2,4-diyl)bis(9H-carbazole), 0.04 g (0.03 mmol) of Pd(PPh$_3$)$_4$, 3.25 ml of 2M Na$_2$CO$_3$, 10 ml of EtOH and 30 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (1.24 g, 1.50 mmol, 46%) as a pale yellow solid. 1H NMR(CDCl3, 400 MHz): chemical shift(ppm) 9.08(s, 1H), 8.97~8.77(m, 3H), 8.53~8.29(m, 8H), 7.92~7.78(m, 7H), 7.63~7.43(m, 14H), 1.69(s, 6H). MS(m/z, FAB$^+$): 831.0

Example 6

Synthesis of EX37

Synthesis of 9,9'-(2-(3-(10,10-dimethyl-10H-indeno[2,1-b]triphenylen-6-yl)phenyl)pyrimidine-4,6-diyl)bis(9H-carbazole)

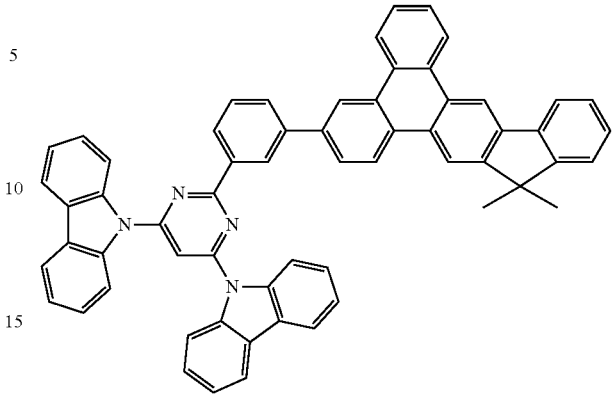

9,9'-(2-(3-bromophenyl)pyrimidine-4,6-diyl)bis(9H-carbazole) instead of 9,9'-(6-(4-bromophenyl)-1,3,5-triazine-2,4-diyl)bis(9H-carbazole), except for using the same method as in synthesis Example 5, the desired compound of 9,9'-(2-(3-(10,10-dimethyl-10H-indeno[2,1-b]triphenylen-6-yl)phenyl)pyrimidine-4,6-diyl)bis(9H-carbazole)(1.18 g, yield=44%) was obtained. MS(m/z, FAB$^+$):829.8

Example 7

Synthesis of EX38

Synthesis of 9,9'-(2-(3-(10,10-dimethyl-10H-indeno[2,1-b]triphenylen-6-yl)phenyl)pyrimidine-4,6-diyl)bis(9H-carbazole)

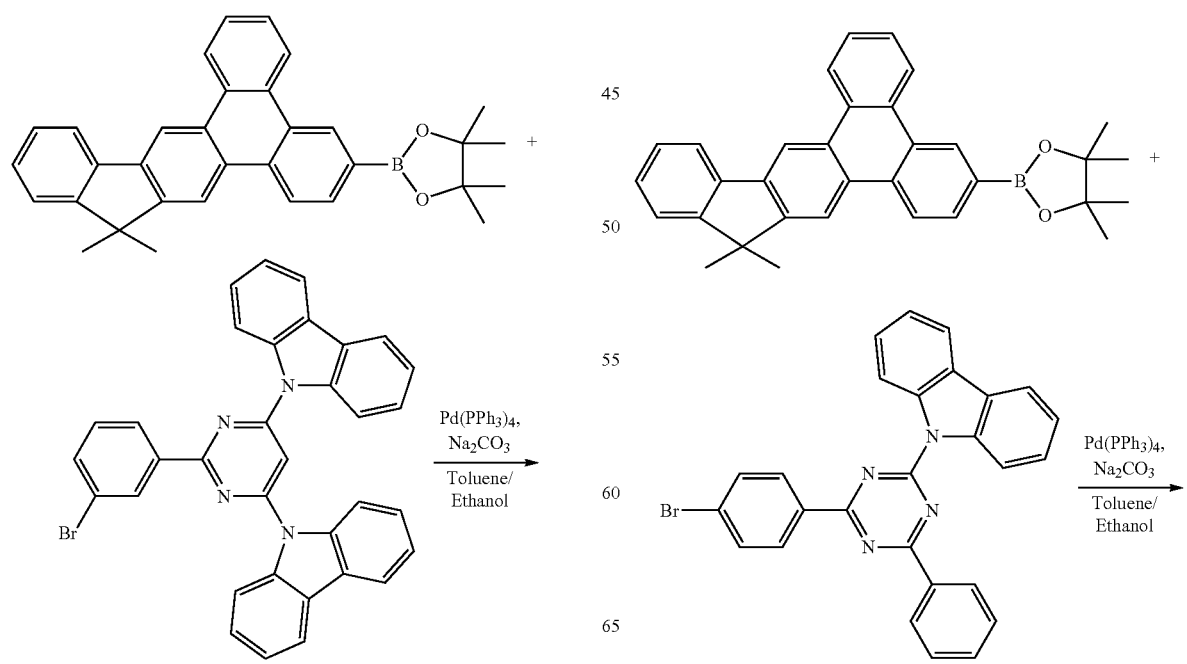

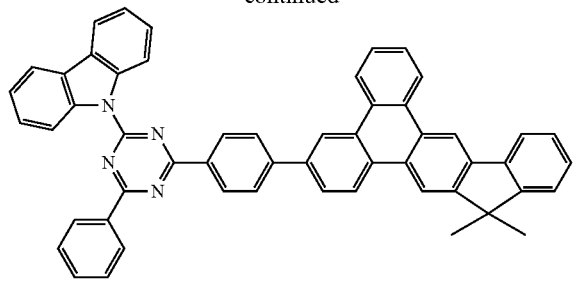

9-(4-(4-bromophenyl)-6-phenyl-1,3,5-triazin-2-yl)-9H-carbazole instead of 9,9'-(6-(4-bromophenyl)-1,3,5-triazine-2,4-diyl)bis(9H-carbazole) except for using the same method as in synthesis Example 5, the desired compound of 9-(4-(4-(10,10-dimethyl-10H-indeno[2,1-b]triphenylen-6-yl)phenyl)-6-phenyl-1,3,5-triazin-2-yl)-9H-carbazole (1.20 g, yield=50%) was obtained. MS(m/z, FAB+):741.5

Example 8

Synthesis of EX42

Synthesis of 9-(4-(10,10-dimethyl-10H-indeno[2,1-b]triphenylen-6-yl)phenyl)-9H-carbazole

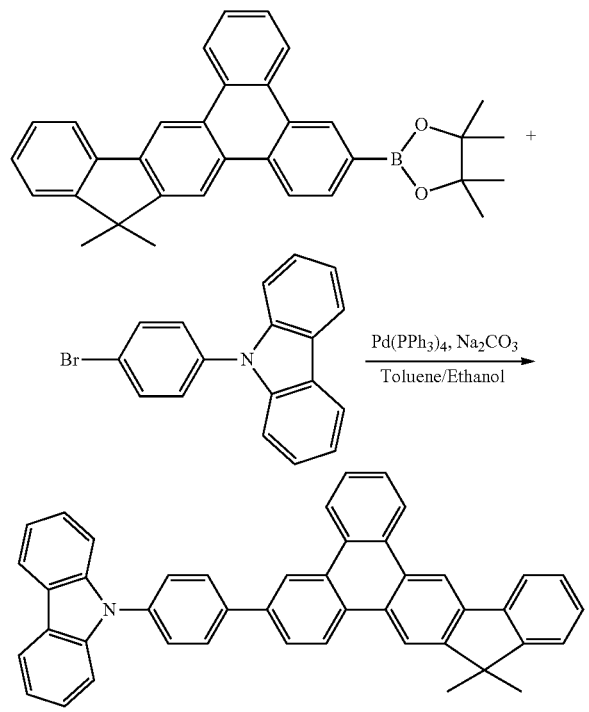

A mixture of 2 g(4.25 mmol) of 2-(10,10-dimethyl-10H-indeno[2,1-b]triphenylen-6-yl)-4,4,5,5-tetramethyl-1,3,2-dioxaborolane, 1.05 g (3.26 mmol) of 9-(4-bromophenyl)-9H-carbazole, 0.04 g(0.03 mmol) of Pd(PPh₃)₄, 3.25 ml of 2M Na₂CO₃, 10 ml of EtOH and 30 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (1.43 g, 2.45 mmol, 75%) as a pale yellow solid. 1H NMR(CDCl3, 400 MHz): chemical shift (ppm) 9.01(s, 1H), 8.82(d, 2H), 8.77(s, 1H), 8.55(s, 1H), 8.49(s, 1H), 7.98(d, 1H), 7.85~7.75 (m, 6H), 7.63~7.33(m, 12H), 1.69(s, 6H). MS(m/z, FAB+): 586.3

Example 9

Synthesis of EX44

Synthesis of 9,9'-(5-(10,10-dimethyl-10H-indeno[2,1-b]triphenylen-6-yl)-1,3-phenylene)bis(9H-carbazole)

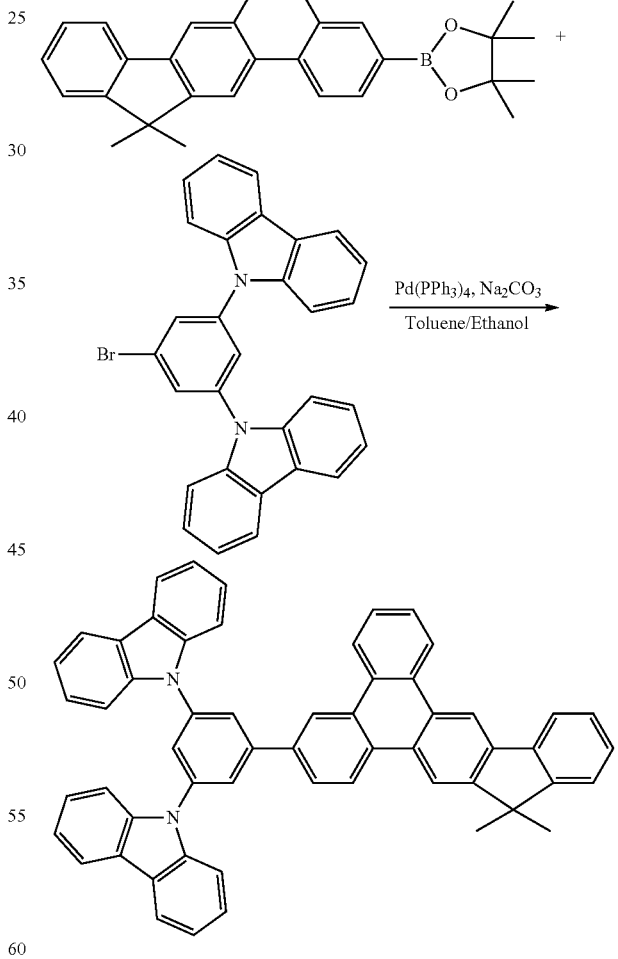

9,9'-(5-bromo-1,3-phenylene)bis(9H-carbazole) instead of 9-(4-bromophenyl)-9H-carbazole, except for using the same method as in synthesis Example 8, the desired compound of 9,9'-(5-(10,10-dimethyl-10H-indeno[2,1-b]triphenylen-6-yl)-1,3-phenylene)bis(9H-carbazole) (1.46 g, yield=60%) was obtained. MS(m/z, FAB+):751.4

Example 10

Synthesis of EX50

Synthesis of 9-(4-(10,10-dimethyl-10H-indeno[2,1-b]triphenylen-6-yl)phenyl)-9'-phenyl-9H,9'H-3,3'-bicarbazole

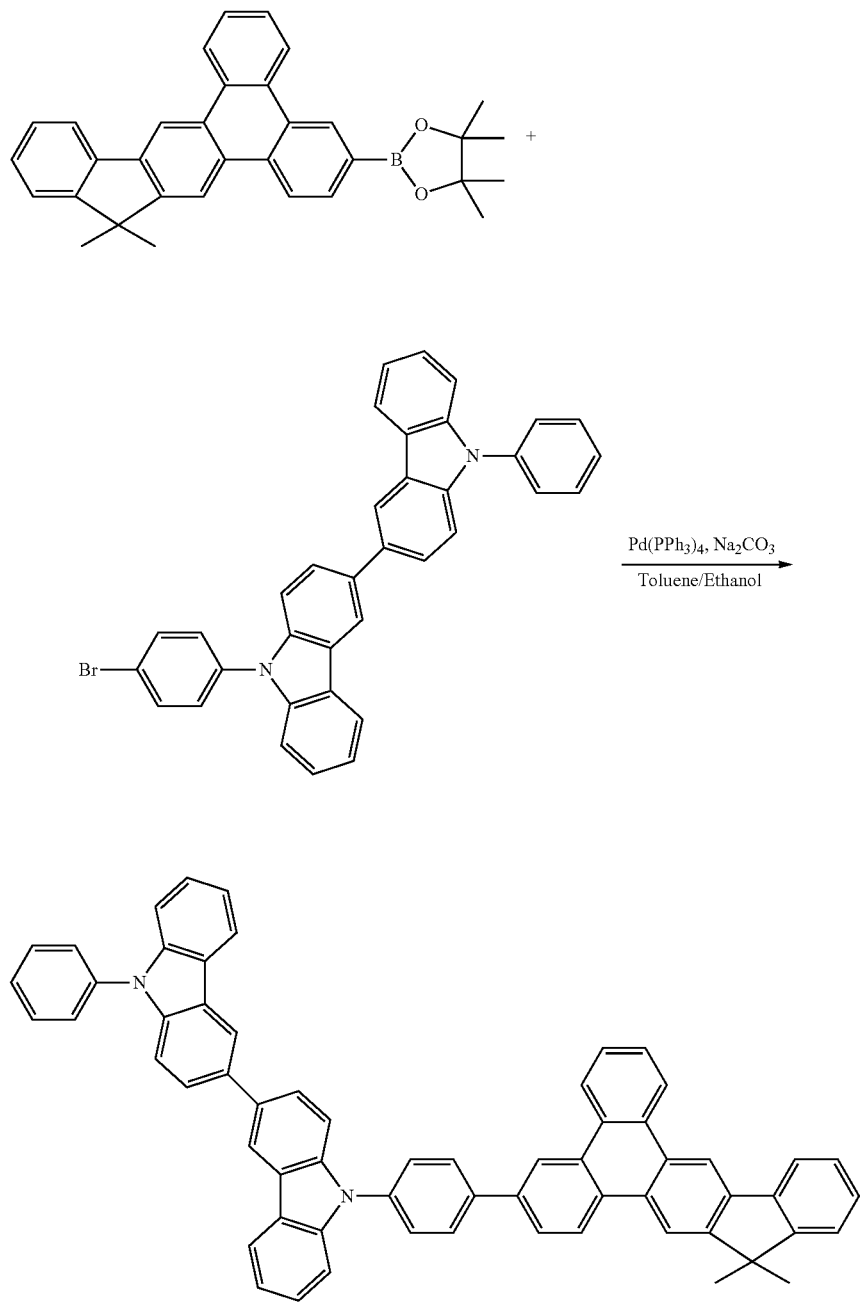

9-(4-bromophenyl)-9'-phenyl-9H,9'H-3,3'-bicarbazole instead of 9-(4-bromophenyl)-9H-carbazole, except for using the same method as in synthesis Example 8, the desired compound of 9-(4-(10,10-dimethyl-10H-indeno[2,1-b]triphenylen-6-yl)phenyl)-9'-phenyl-9H,9'H-3,3'-bicarbazole (1.28 g, yield=48%) was obtained. MS(m/z, FAB$^+$): 827.9

Example 11

Synthesis of EX51

Synthesis of 3-(3-(10,10-dimethyl-10H-indeno[2,1-b]triphenylen-6-yl)phenyl)-9-phenyl-9H-carbazole

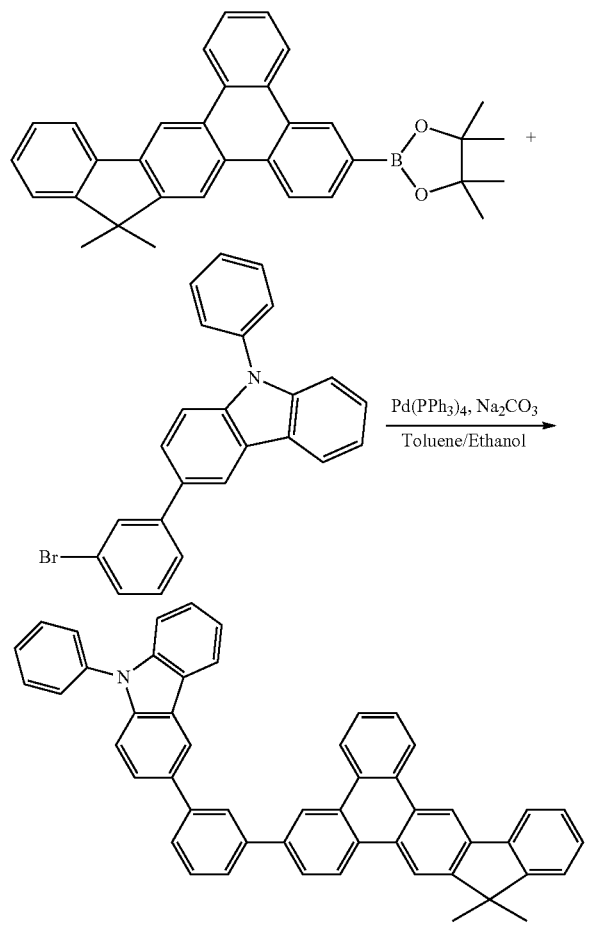

3-(3-bromophenyl)-9-phenyl-9H-carbazole instead of 9-(4-bromophenyl)-9H-carbazole, except for using the same method as in synthesis Example 8, the desired compound of 3-(3-(10,10-dimethyl-10H-indeno[2,1-b]triphenylen-6-yl)phenyl)-9-phenyl-9H-carbazole (1.28 g, yield=48%) was obtained. MS(m/z, FAB+):662.7

Example 12

Synthesis of EX55

Synthesis of 4-(3-(10,10-dimethyl-10H-indeno[2,1-b]triphenylen-6-yl)phenyl)dibenzo[b,d]thiophene

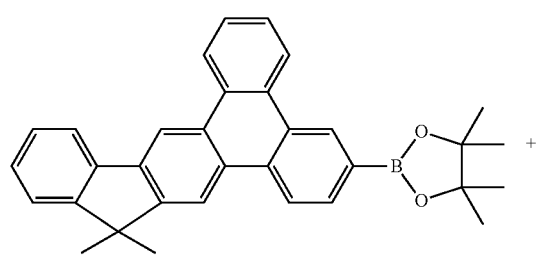

-continued

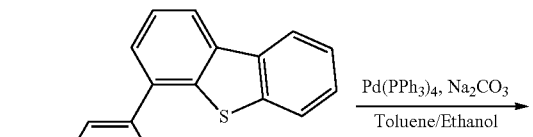

A mixture of 2 g(4.25 mmol) of 2-(10,10-dimethyl-10H-indeno[2,1-b]triphenylen-6-yl)-4,4,5,5-tetramethyl-1,3,2-dioxaborolane, 1.10 g (3.26 mmol) of 4-(3-bromophenyl)dibenzo[b,d]thiophene, 0.04 g (0.03 mmol) of Pd(PPh$_3$)$_4$, 3.25 ml of 2M Na$_2$CO$_3$, 10 ml of EtOH and 30 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (1.62 g, 2.6 mmol, 80%) as a pale yellow solid. 1H NMR (CDCl3, 400 MHz): chemical shift (ppm) 9.03(s, 1H), 8.86(d, 2H), 8.70(s, 1H), 8.49(s, 1H), 8.46(s, 1H), 7.96(d, 1H), 7.85~7.76(m, 2H), 7.68~7.25(m, 15H), 1.69(s, 6H). MS(m/z, FAB+): 603.5

Example 13

Synthesis of EX56

Synthesis of 2,2'-(5-(10,10-dimethyl-10H-indeno[2,1-b]triphenylen-6-yl)-1,3-phenylene)didibenzo[b,d]furan

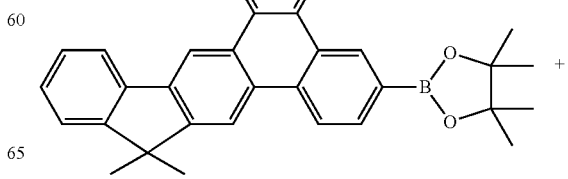

-continued

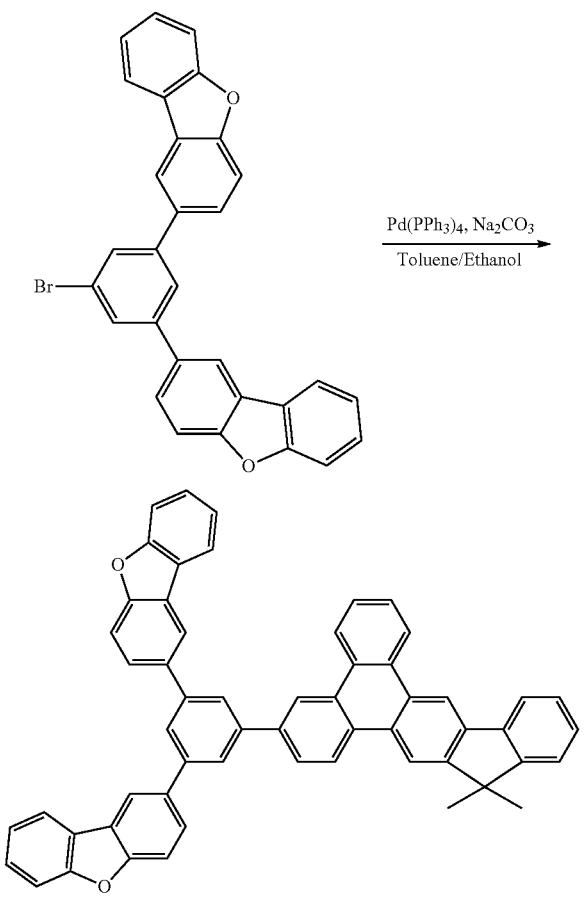

2,2'-(5-bromo-1,3-phenylene)didibenzo[b,d]furan instead of 4-(3-bromophenyl)dibenzo[b,d]thiophene, except for using the same method as in synthesis Example 12, the desired compound of 2,2'-(5-(10,10-dimethyl-10H-indeno[2,1-b]triphenylen-6-yl)-1,3-phenylene)didibenzo[b,d]furan (1.30 g, yield=53%) was obtained. MS(m/z, FAB+):752.9

Example 14

Synthesis of EX57

Synthesis of 4-(3'-(10,10-dimethyl-10H-indeno[2,1-b]triphenylen-6-yl)biphenyl-3-yl)dibenzo[b,d]thiophene

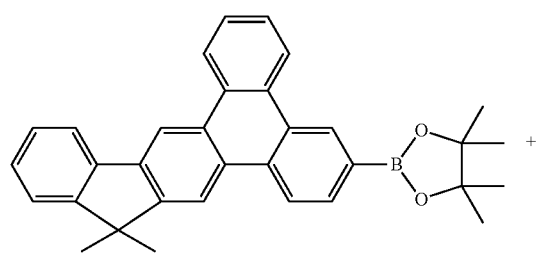

-continued

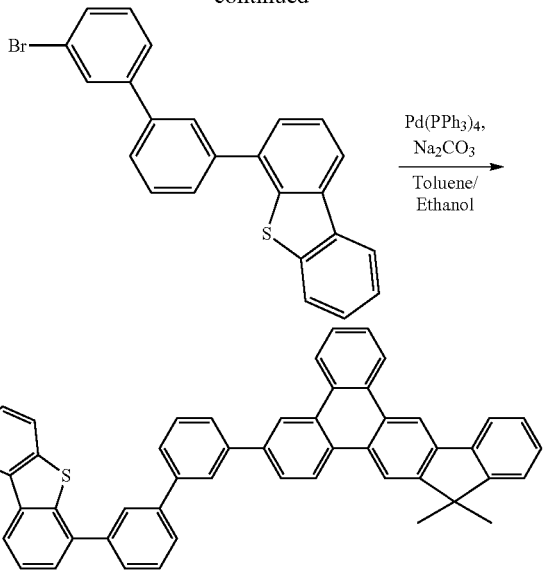

4-(3'-bromobiphenyl-3-yl)dibenzo[b,d]thiophene instead of 4-(3-bromophenyl)dibenzo[b,d]thiophene, except for using the same method as in synthesis Example 12, the desired compound of 4-(3'-(10,10-dimethyl-10H-indeno[2,1-b]triphenylen-6-yl)biphenyl-3-yl)dibenzo[b,d]thiophene (1.30 g, yield=53%) was obtained. MS(m/z, FAB+):679.5

General Method of Producing Organic El Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, N,N-Bis(naphthalene-1-yl)-N,N-bis(phenyl)-benzidine(NPB) is most widely used as the hole transporting layer. 10,10-dimethyl-12-(10-(naphthalen-2-yl)anthracen-9-yl)-10H-indeno[2,1-b]triphenylene(H1) is used as blue emitting host and N1,N1,N6,N6-tetram-tolylpyrene-1,6-diamine(D1) is used as blue guest. 2-(10,10-dimethyl-10H-indeno[2,1-b]triphenylen-13-yl)-4,6-diphenyl pyrimidine(HB1) is used as hole blocking material(HBM) and 4,7-Diphenyl-2,9-bis(4-(1-phenyl-1H-benzo[d]imidazole-2-yl)phenyl)-1,10-phenanthroline (LT-N8001, U.S. Pat. No. 7,754,348) is used as electron transporting material (ETM) to co-deposit with 8-hydroxyquinolato-lithium (LiQ) in organic EL device. Bis(2-methyl-8-quinolinolate)-4-(phenylphenolato)aluminium(BAlq) is used as hole blocking material(HBM) or phosphorescent host for phosphorescent system, Bis(2-phenylpyridinato) (2,4-diphenylpyridinato) iridium(III) (D2) is used as phosphorescent dopant. The prior art of OLED materials for producing standard organic EL device control and comparable material in this invention shown its chemical structure as following formulas:
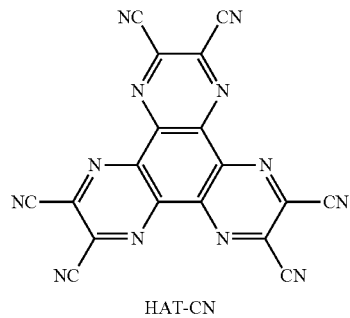
HAT-CN
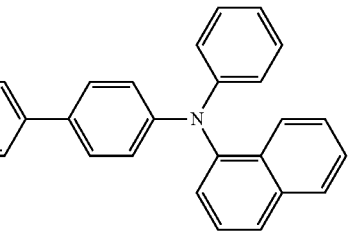
NPB
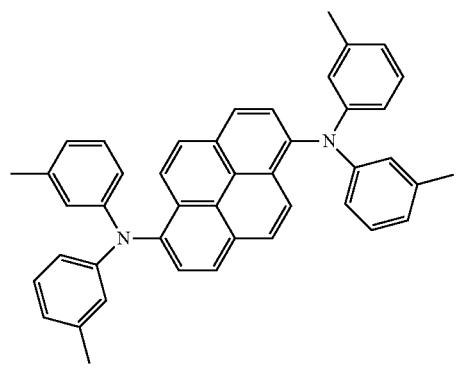
D1
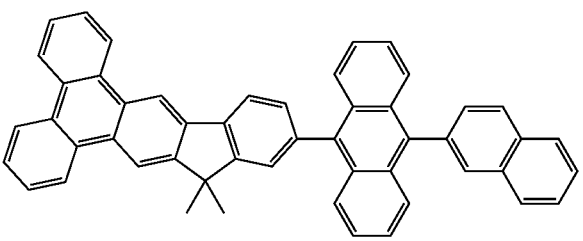
H1
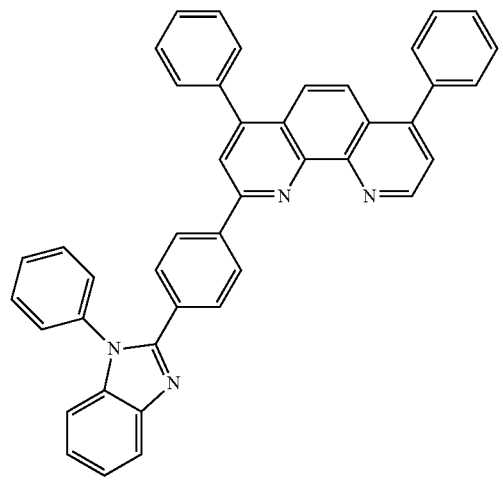
LT-N8001
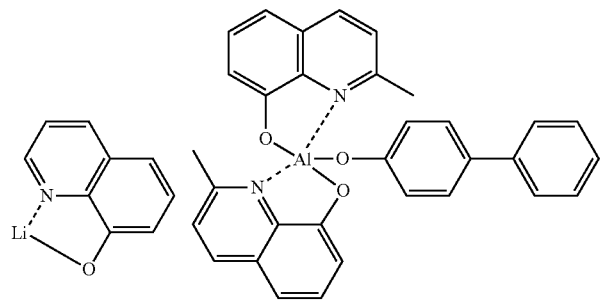
LiQ            BAlq -continued
HB1
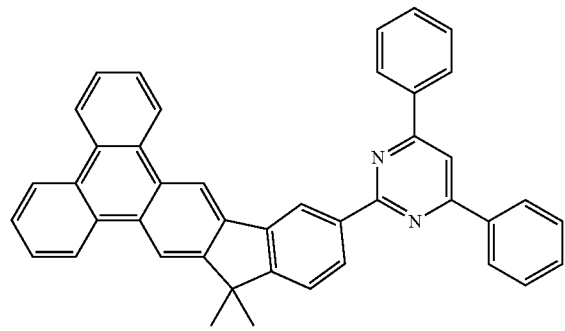
D2
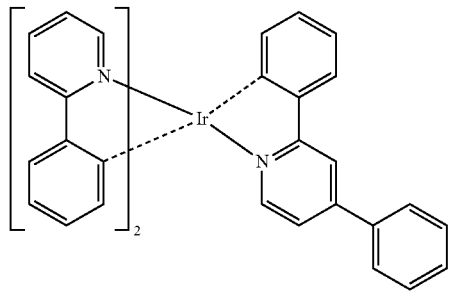
EX5
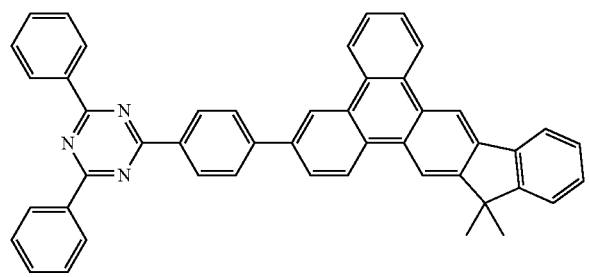
EX9
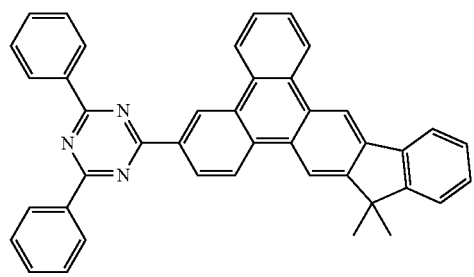
EX10
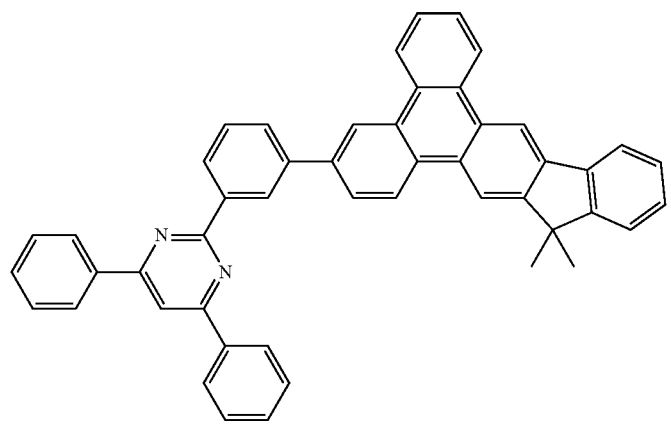
EX15
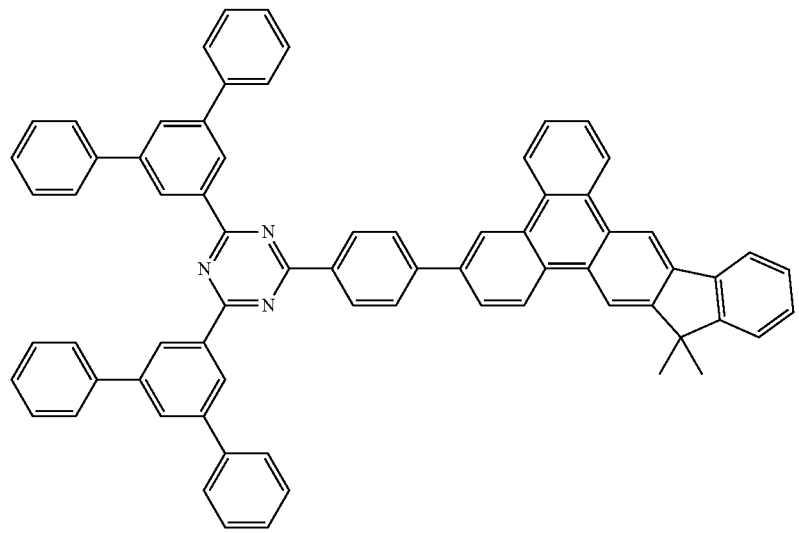

-continued
EX33
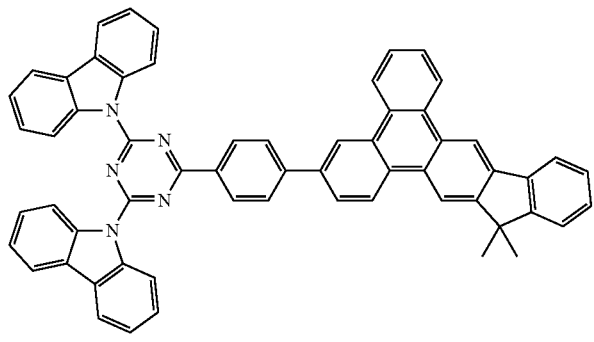
EX37
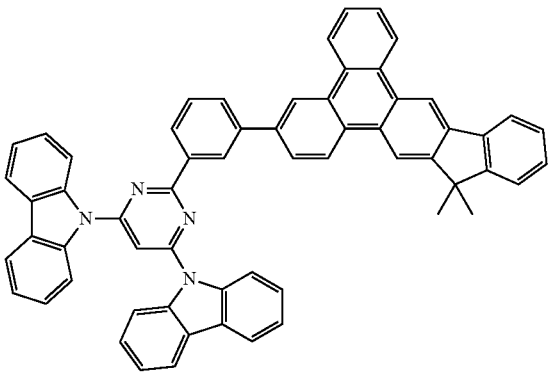
EX38
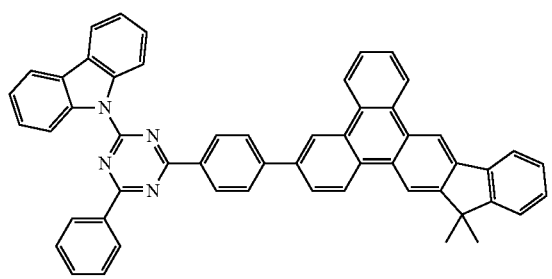
EX42
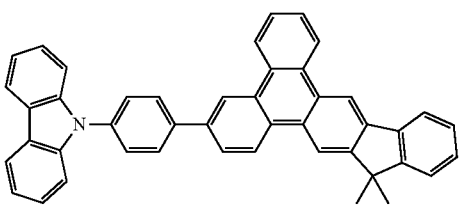
EX44
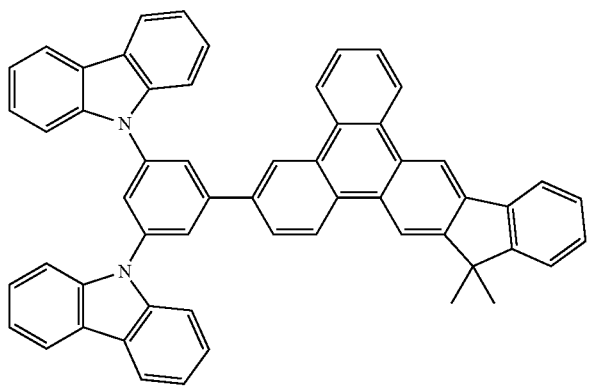
EX50
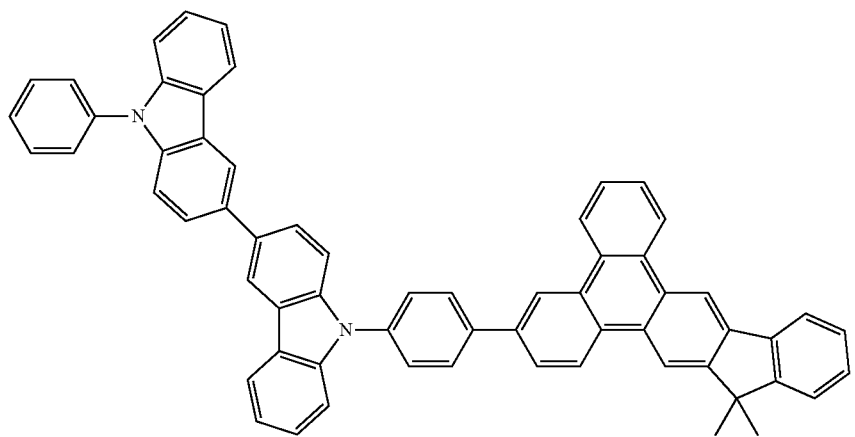

-continued

EX51

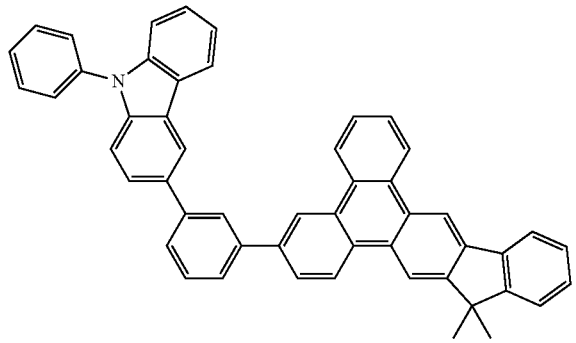

EX55

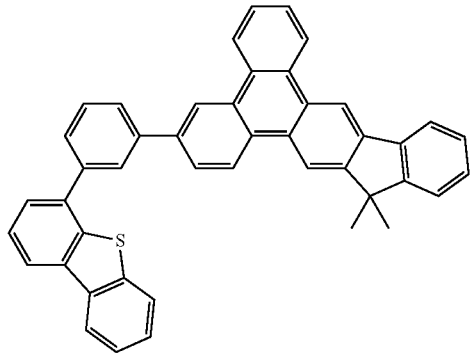

EX56

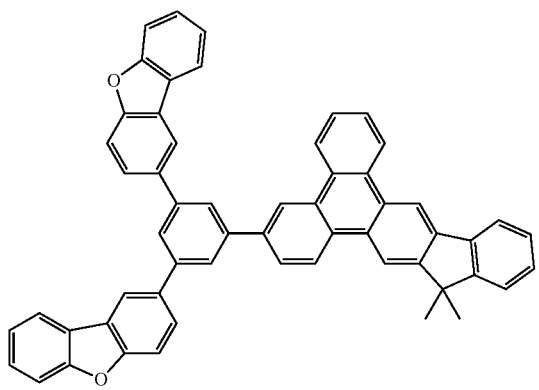

EX57

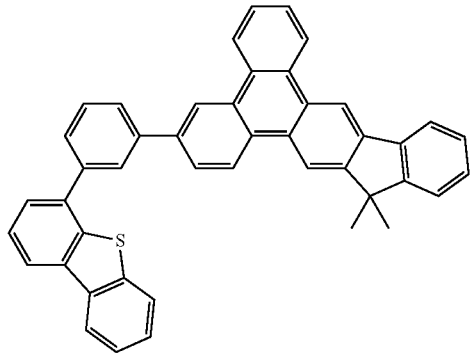

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 15

Using a procedure analogous to the above mentioned general method, fluorescent blue emitting organic EL device having the following device structure were produced (See FIG. 1): ITO/HAT-CN(20 nm)/NPB(130 nm)/H1 doped 5% D1 (30 nm)/HBM(10 nm)/ETM co-deposit LiQ (ETM:LiQ, ratio=1:1 (40 nm)/LiQ(1 nm)/Al (160 nm). The I-V-B (at 1000 nits) and half-life time of fluorescent blue-emitting organic EL device testing report as Table 1, The half-life time is defined that the initial luminance of 1000 cd/m² has dropped to half.

TABLE 1

| HBM | ETM | Voltage (V) | Efficiency (cd/A) | CIE (y) | Half-lifetime (hour) |
|---|---|---|---|---|---|
| HB1 | LT-N8001 | 6.5 | 4.3 | 0.174 | 340 |
| BAlq | LT-N8001 | 7.2 | 3.9 | 0.174 | 220 |
| HB1 | EX5 | 5.5 | 6.7 | 0.180 | 350 |
| HB1 | EX9 | 5.8 | 5.5 | 0.183 | 180 |
| HB1 | EX10 | 5.4 | 6.5 | 0.180 | 450 |
| HB1 | EX15 | 5.6 | 6.0 | 0.181 | 320 |
| BAlq | EX10 | 7.5 | 5.3 | 0.174 | 250 |
| — | EX10 | 5.1 | 6.8 | 0.183 | 390 |
| BAlq | EX5 | 7.7 | 6.4 | 0.177 | 230 |

Example 16

Using a procedure analogous to the above mentioned general method, phosphorescent emitting organic EL device having the following device structures are produced (See FIG. 1): ITO/HAT-CN (20 nm)/NPB(130 nm)/phosphorescent host(PHhost)+15% D2 (30 nm)/HBM(15 nm)/EX5 co-deposit LiQ (EX5: LiQ, ratio=1:1)(40 nm)/LiQ (1 nm)/Al (160 nm). The I-V-B (at 1000 nits) and half-life time of phosphorescent emitting organic EL device testing report as Table 2. The half-life time is defined that the initial luminance of 3000 cd/m² has dropped to half.

TABLE 2

| PHhost(H1 + H2) H1:H2 = 1:1 | HBM | Voltage (V) | Efficiency (lm/w) | CIE (x, y) | Half-life time (hour) |
|---|---|---|---|---|---|
| BAlq | BAlq | 6.8 | 16 | 0.44, 0.56 | 380 |
| EX37 + EX50 | BAlq | 5.3 | 28 | 0.44, 0.56 | 450 |
| EX37 + EX50 | HB1 | 2.8 | 45 | 0.41, 0.54 | 650 |
| EX37 + EX55 | HB1 | 2.5 | 48 | 0.41, 0.54 | 650 |
| EX37 + EX56 | HB1 | 2.5 | 40 | 0.41, 0.53 | 600 |
| EX37 + EX57 | HB1 | 2.5 | 42 | 0.41, 0.54 | 650 |
| EX37 + EX42 | HB1 | 3.0 | 38 | 0.41, 0.53 | 660 |
| EX37 + EX44 | HB1 | 2.8 | 34 | 0.40, 0.53 | 550 |
| EX37 + EX51 | HB1 | 3.2 | 32 | 0.41, 0.54 | 560 |
| EX33 + EX50 | HB1 | 2.5 | 46 | 0.41, 0.55 | 600 |
| EX38 + EX50 | HB1 | 2.8 | 49 | 0.41, 0.55 | 720 |
| EX33 | HB1 | 2.5 | 36 | 0.42, 0.56 | 480 |
| EX37 | HB1 | 2.6 | 31 | 0.43, 0.55 | 500 |
| EX55 | HB1 | 3.2 | 40 | 0.43, 0.54 | 460 |
| EX57 | HB1 | 3.0 | 42 | 0.42, 0.54 | 550 |

In the above preferred embodiments for organic EL device test report (see Table 1 and Table 2), we show that the organic material formula (I) in the present invention used as hole blocking material, electron transport material and/or phosphorescent host display good performance than the prior art of organic EL materials.

To sum up, the present invention discloses a novel organic material which can be used for organic EL device is disclosed. The mentioned organic material are represented by the following formula (I):

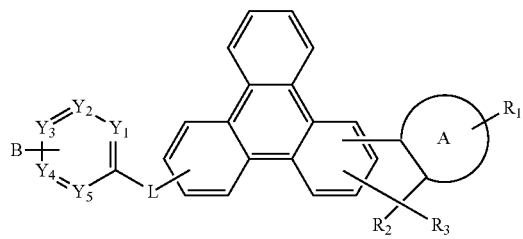

formula(I)

wherein A ring represents a phenyl group and fused ring hydrocarbon units with two to four rings group, L represents a single bond, a substituted or unsubstituted divalent arylene group having 6 to 30 ring carbon atoms or a substituted or unsubstituted divalent heteroarylene group having 6 to 30 ring carbon atoms, $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms, $Y_1$ to $Y_5$ each independently represent nitrogen atom or $CR_5$, $R_5$ independently represent a hydrogen atom, a substituted or unsubstituted phenylene group having 6 to 30 ring carbon atoms, or a bond linked to B; B stand for a group of following formula (II):

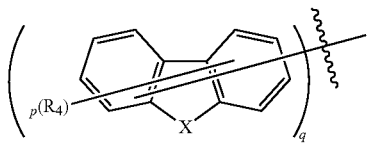

formula(II)

wherein q represents an integer of 0 to 3, p represents an integer of 0 to 7, X represents O, S, $NR_6$, $R_6$ independently represents a hydrogen atom, a substituted or unsubstituted phenyl group, a substituted or unsubstituted carbazole group, and a bond linked to formula (I), $R_4$ is the same definition as $R_1$.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A organic material represented by the following formula(I):

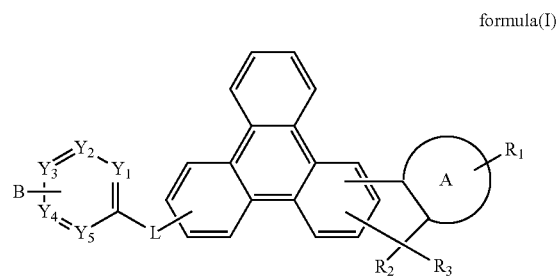

formula(I)

wherein A ring represents a phenyl group and fused ring hydrocarbon units with two to four rings group, L represents a single bond, a substituted or unsubstituted divalent arylene group having 6 to 30 ring carbon atoms or a substituted or unsubstituted divalent heteroarylene group having 6 to 30 ring carbon atoms, $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms, $Y_1$ to $Y_5$ each independently represent nitrogen atom or $CR_5$, $R_5$ independently represent a hydrogen atom, a substituted or unsubstituted phenylene group having 6 to 30 ring carbon atoms, or a bond linked to B; B stand for a group of following formula(II):

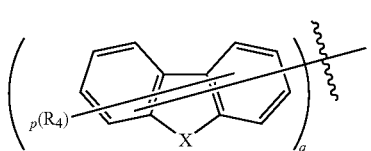

formula(II)

wherein q represents an integer of 1 to 3, p represents an integer of 0 to 7, X represents O, S, $NR_6$, $R_6$, independently represents a hydrogen atom, a substituted or unsubstituted phenyl group, a substituted or unsubstituted carbazole group, and a bond linked to formula(I), $R_4$ is the same definition as $R_1$; with the proviso that when q represents an integer of 1, X represents O or S, A ring represents a phenyl group and L represents a single bond, at least one of $Y_1$ to $Y_5$ represents a nitrogen atom.

2. The organic material according to claim 1, wherein L is one of the following formulas:

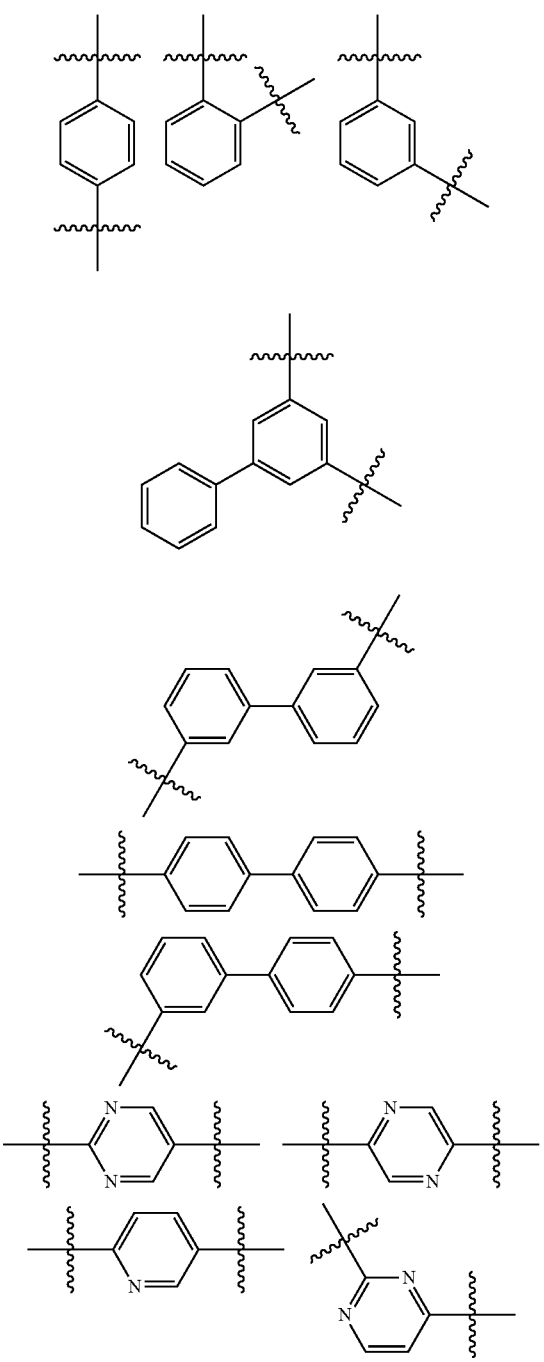

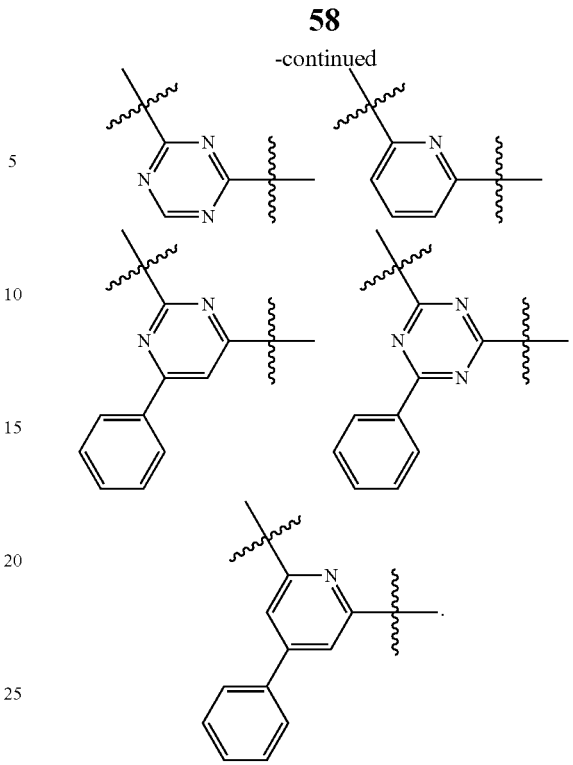

3. The organic material according to claim 1, wherein A ring is selected from the group consisting of naphthyl group, anthracenyl group, phenanthrenyl group, pyrenyl group, chrysenyl group and triphenylene group.

4. A organic electroluminescence device comprising a pair of electrodes consisting of a cathode and an anode, and between the pairs of electrodes comprising at least a light emitting layer, one or more layers of organic thin film layer, wherein the light emitting layer or the organic thin film layer comprising the organic material according to claim 1.

5. The organic electroluminescent device according to claim 4, wherein the emitting layer comprising the organic material with a general formula(I).

6. The organic electroluminescent device according to claim 4, wherein the emitting layer comprising the organic material with a general formula(I) is a phosphorescent host material or thermally activated delayed fluorescence host material.

7. The organic electroluminescent device according to claim 4, wherein the emitting layer comprising phosphorescent dopant or thermally activated delayed fluorescence dopant.

8. The organic electroluminescent device according to claim 4, wherein the phosphorescent dopant are iridium(Ir) complexes.

9. The organic electroluminescent device according to claim 4, wherein the electron transport layer comprising the organic material with a general formula(I).

10. The organic electroluminescent device according to claim 4, wherein the electron transport layer comprising Li, Ca or 8-hydroxyquinolinolato-lithium.

11. The organic electroluminescent device according to claim 4, wherein the hole blocking layer comprising the organic material with a general formula(I).

12. The organic electroluminescence device according to claim 4, wherein the light emitting layer emits phosphorescent green, yellow and red lights.

13. The organic electroluminescence device according to claim 4, wherein the device is an organic light emitting device.

14. The organic electroluminescent device according to claim 4, wherein the device is a lighting panel.

15. The organic electroluminescent device according to claim 4, wherein the device is a backlight panel.

16. An organic compound with one of the following formulas:

EX1

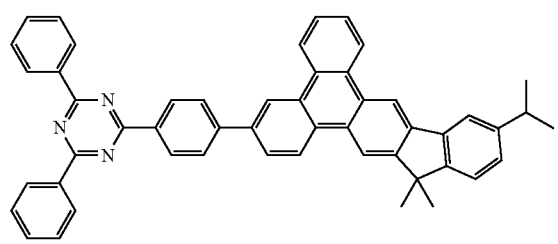

EX2

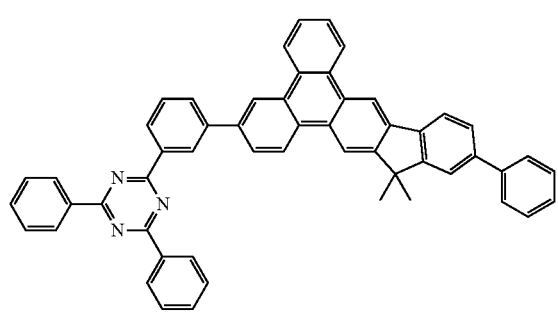

EX3

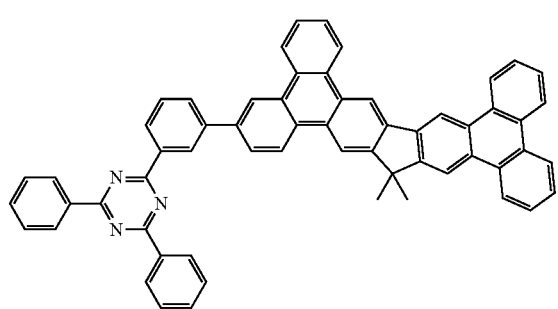

EX4

-continued

EX6

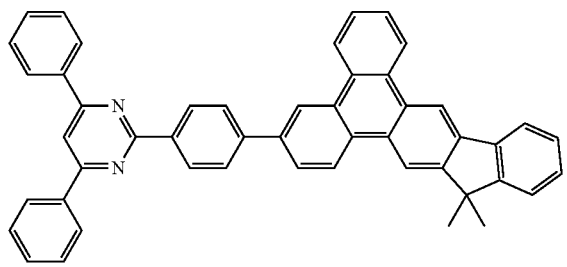

EX7

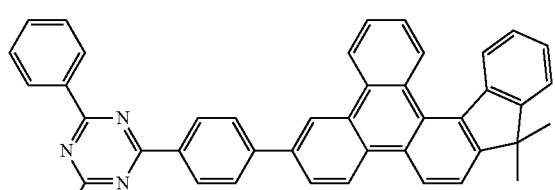

EX8

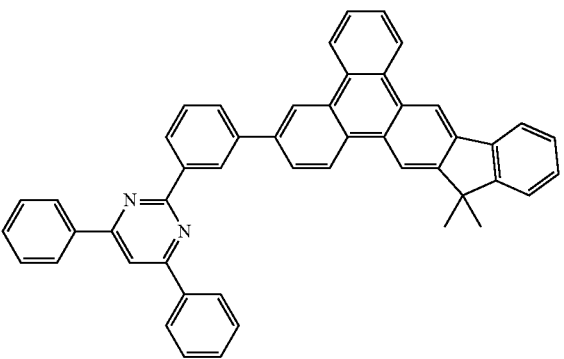

EX10

EX11
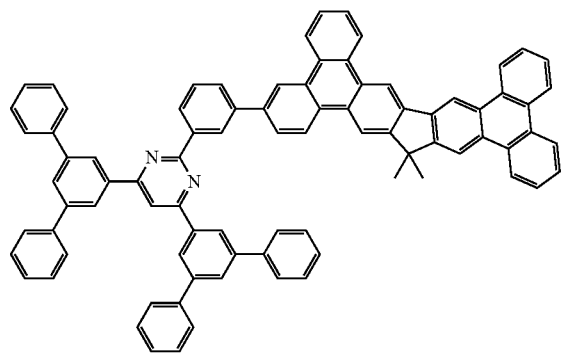
EX12
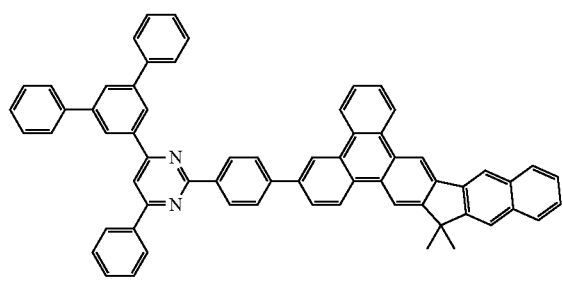
EX13
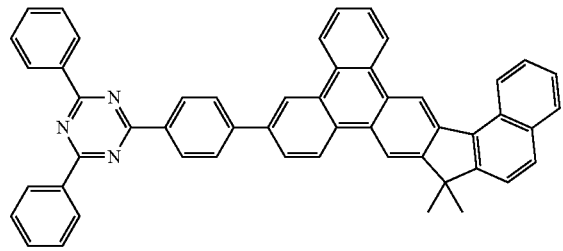
EX14
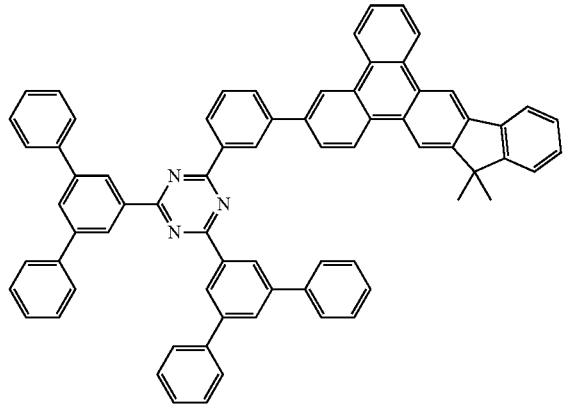
EX15
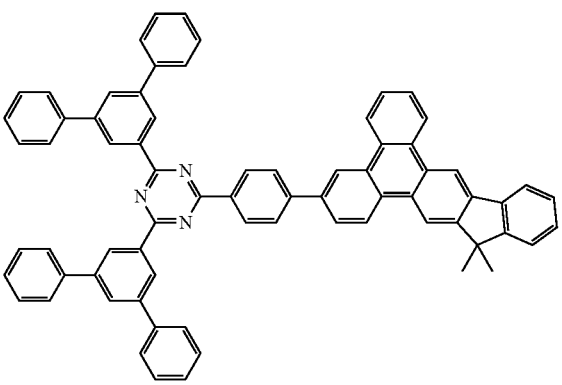
EX16
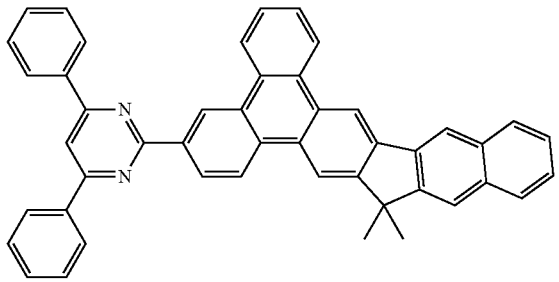
EX17
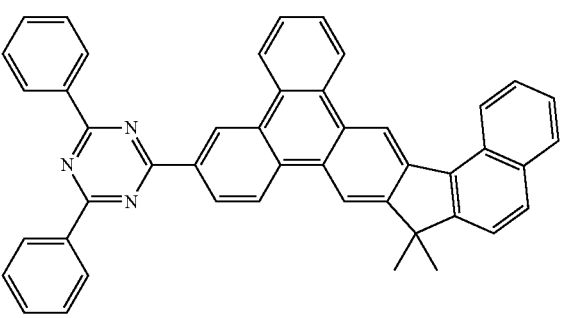
EX18
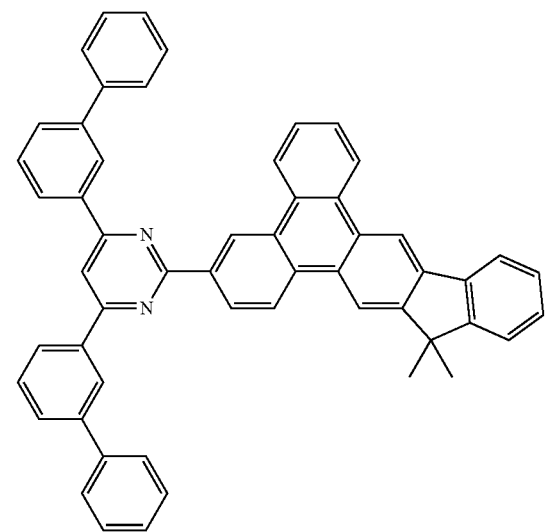

-continued
EX19
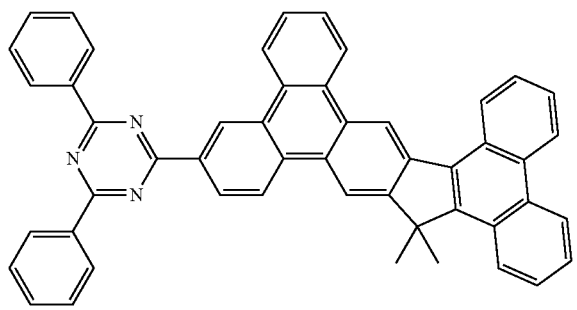
EX20
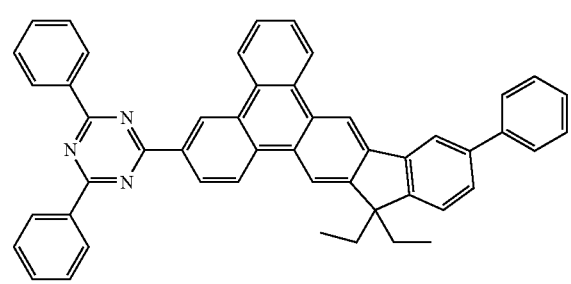
EX21
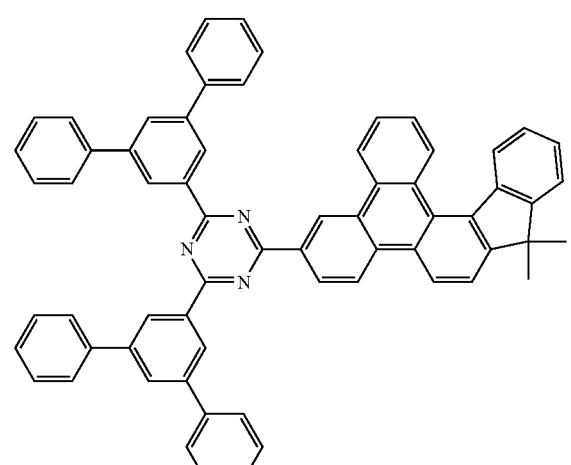
EX22
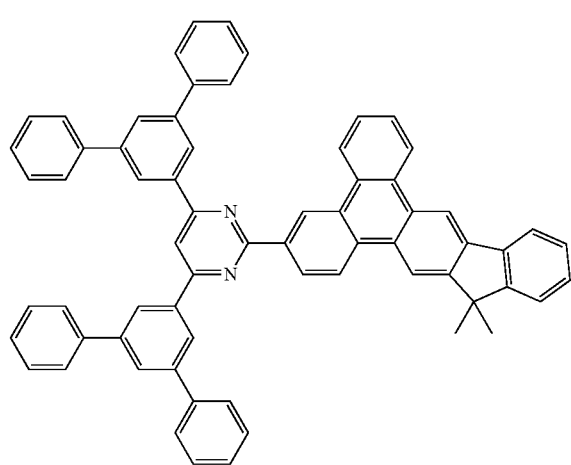
-continued
EX23
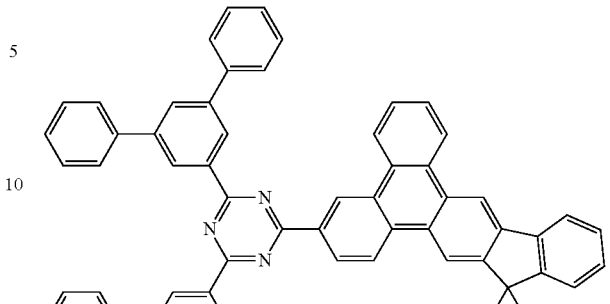
EX24
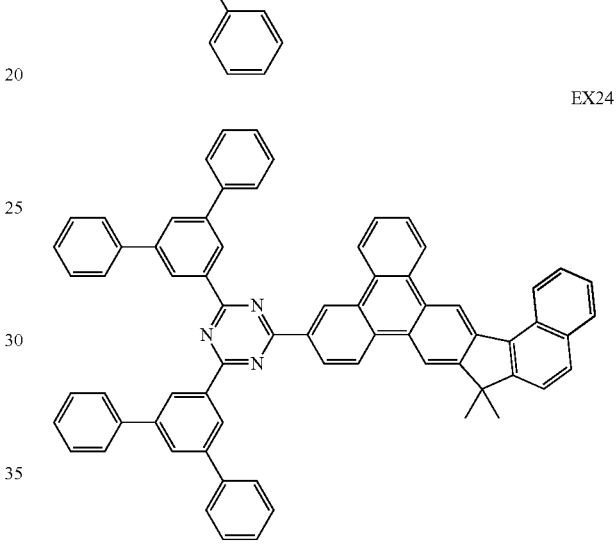
EX25
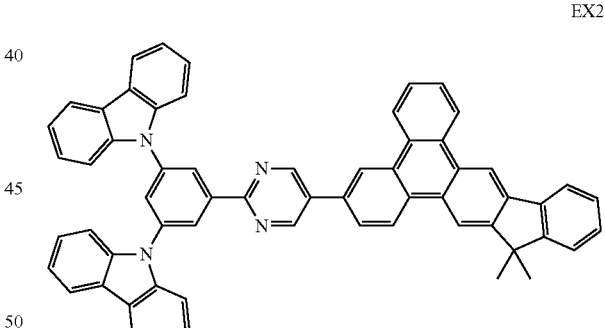
EX26
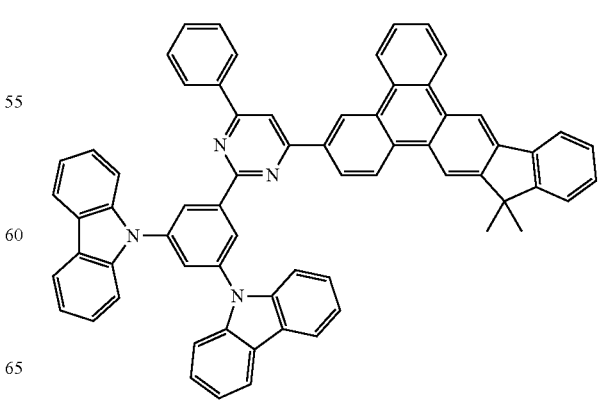

EX27
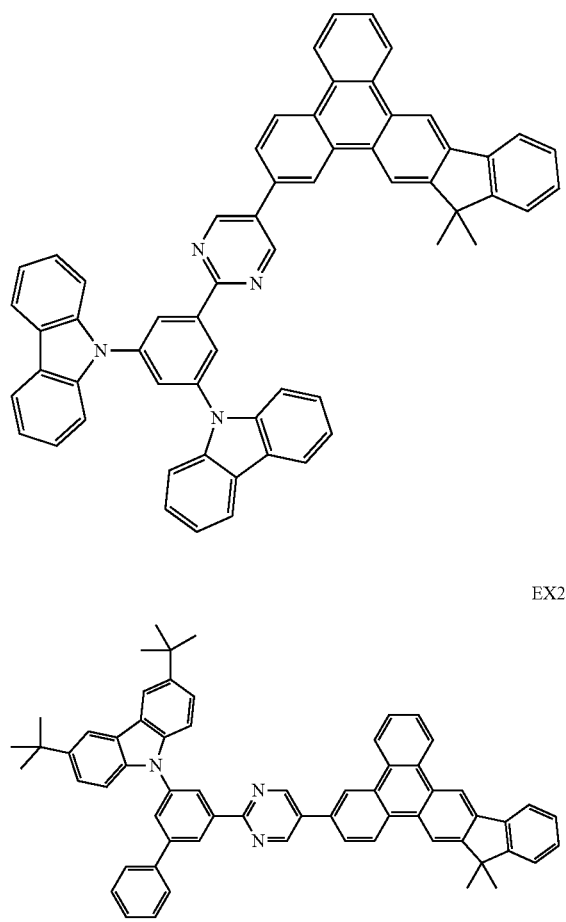
EX28
EX29
EX30
EX31
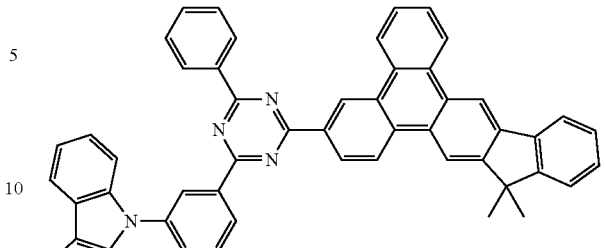
EX32
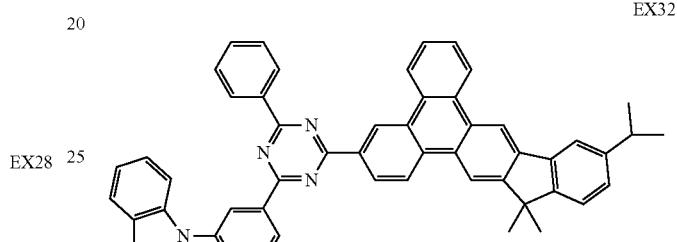
EX33
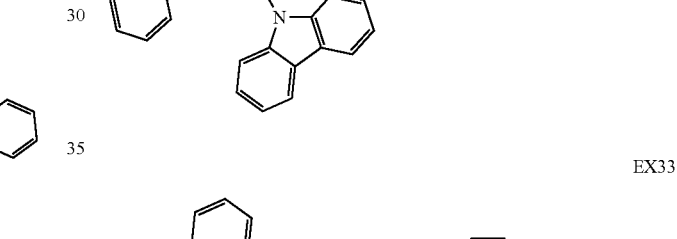
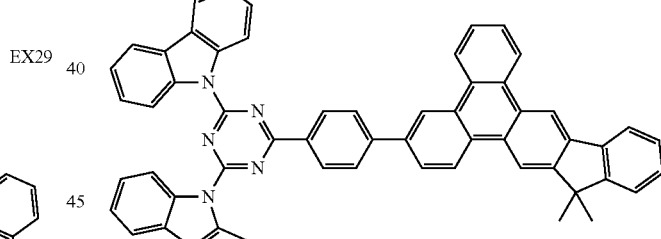
EX34
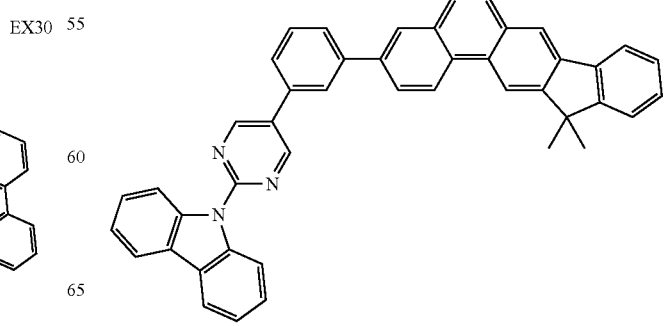

-continued
EX35
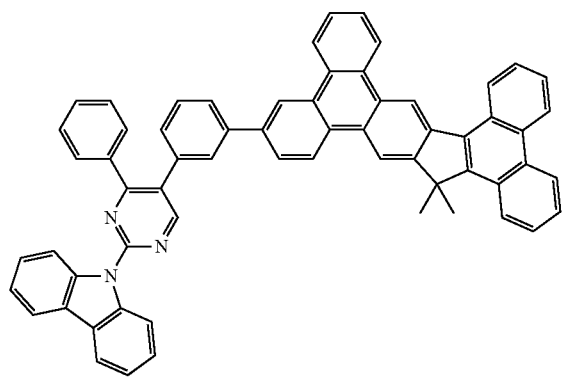
EX36
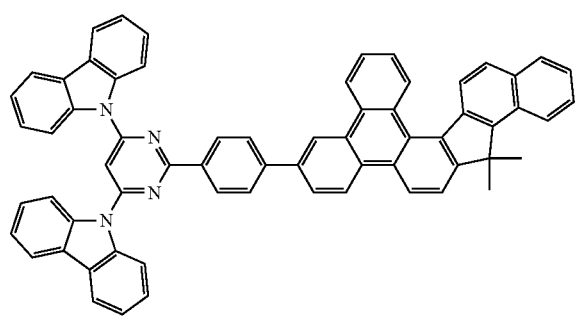
EX37
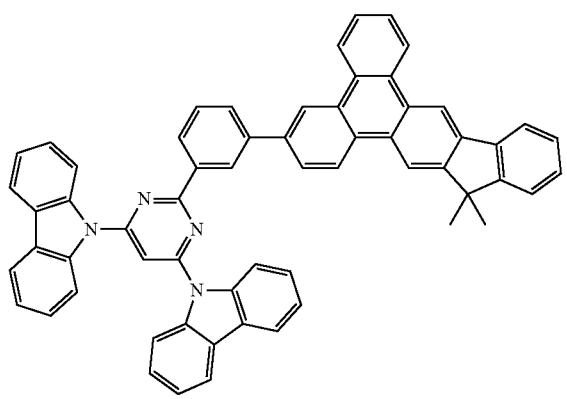
EX38
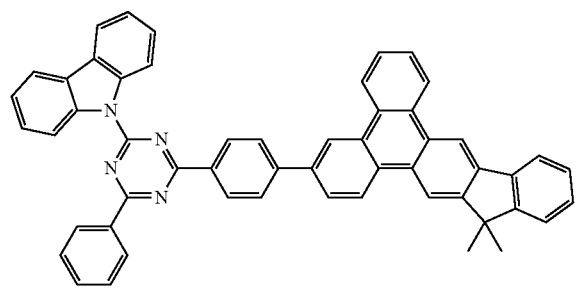
-continued
EX39
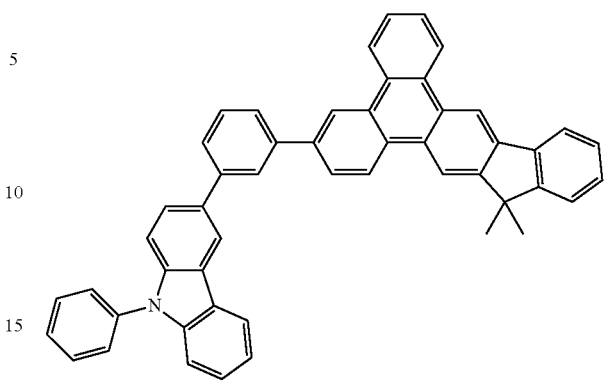
EX40
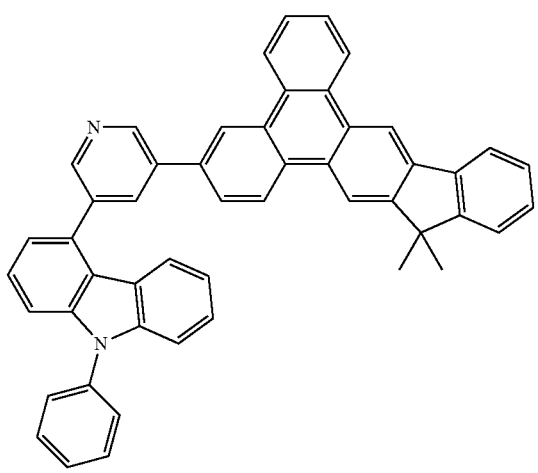
EX41
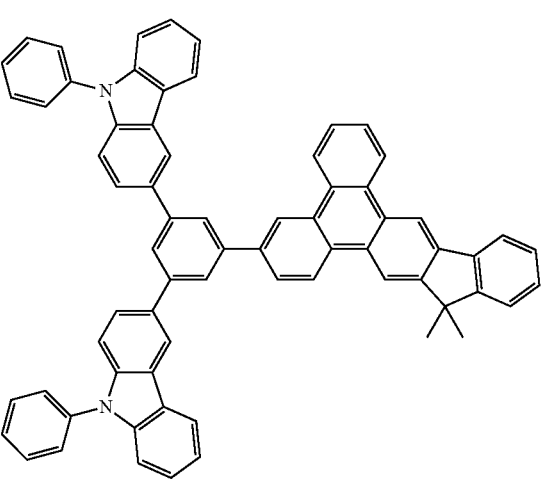
EX42
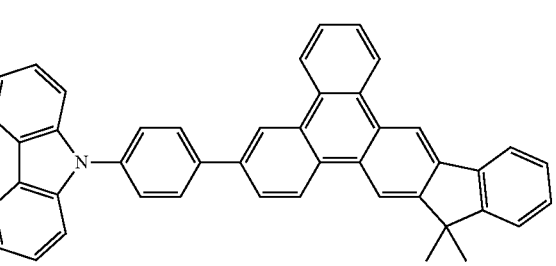

EX43
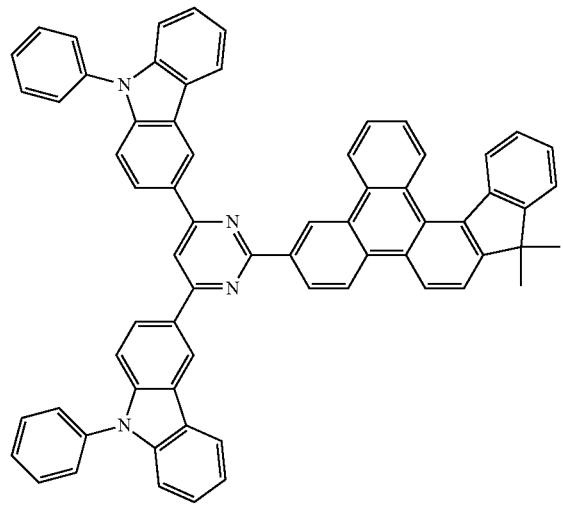
EX44
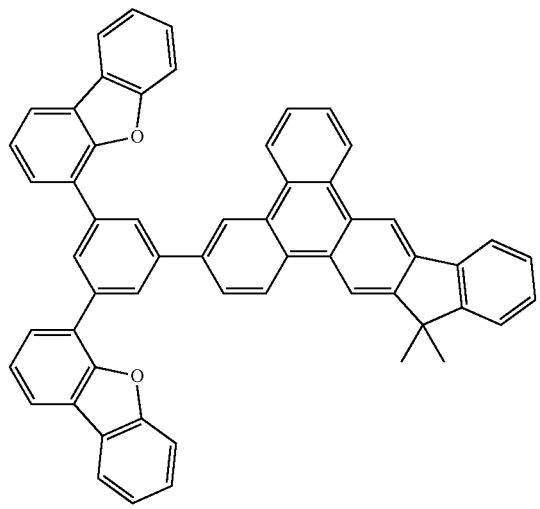
EX47
EX48
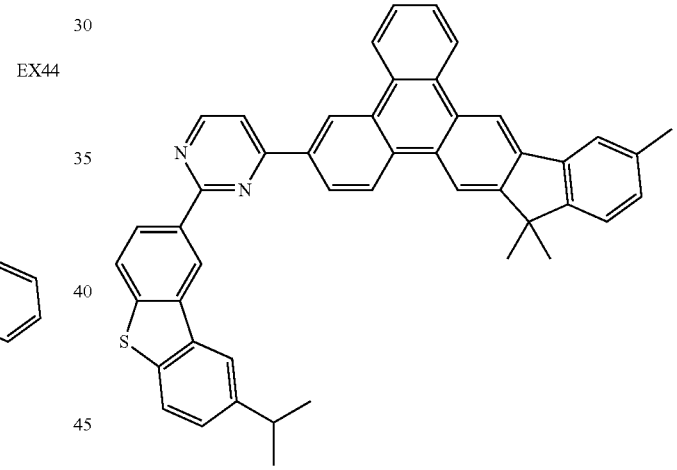
EX45
EX49
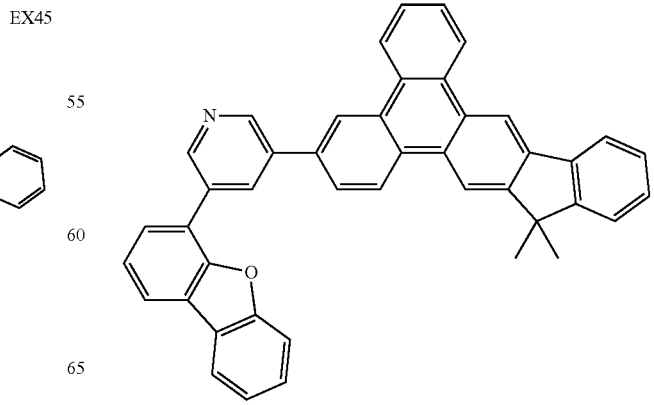

EX50
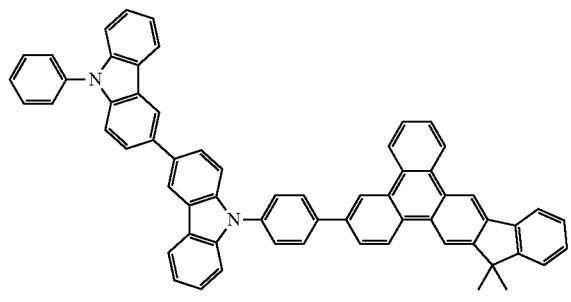
EX51
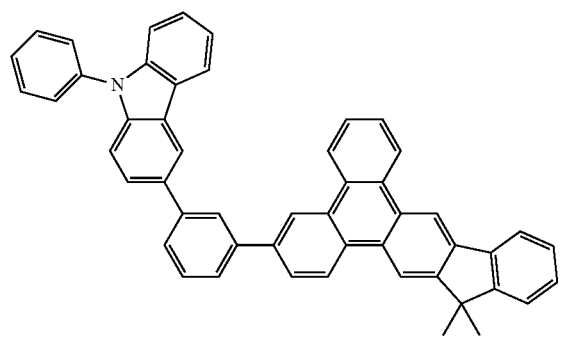
EX52
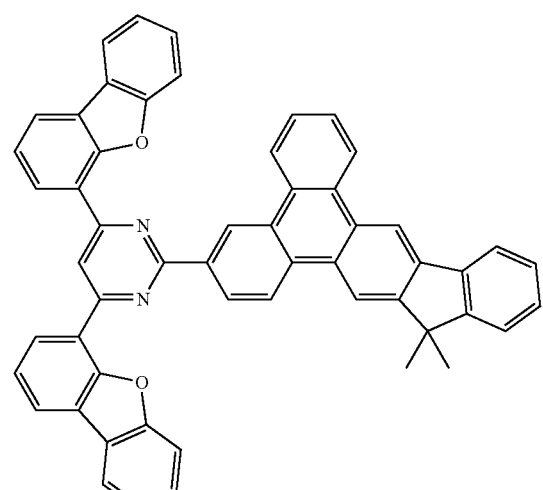
EX53
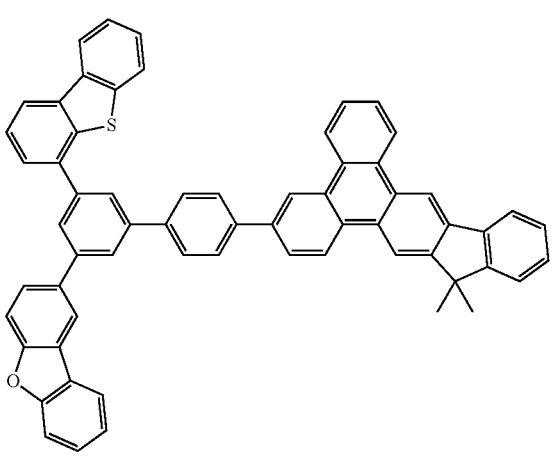
EX54
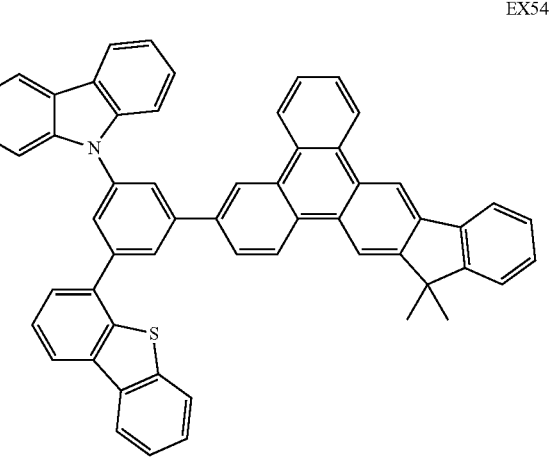
EX56
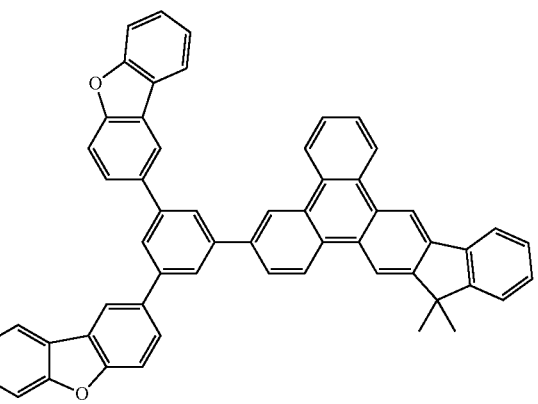
EX57
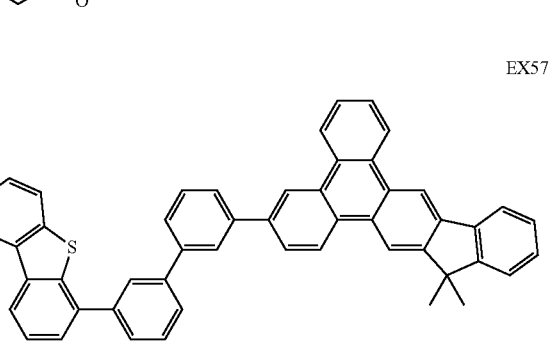
EX58
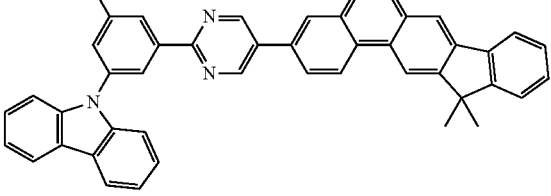

-continued
EX59
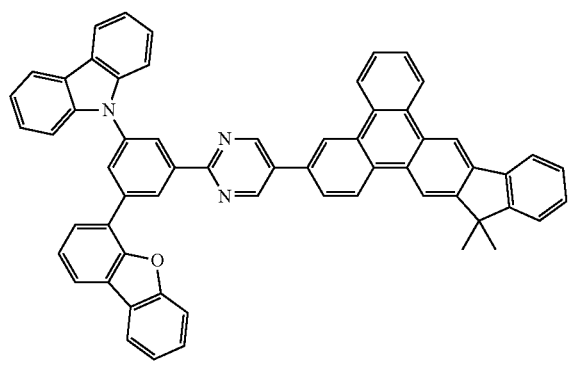
EX60
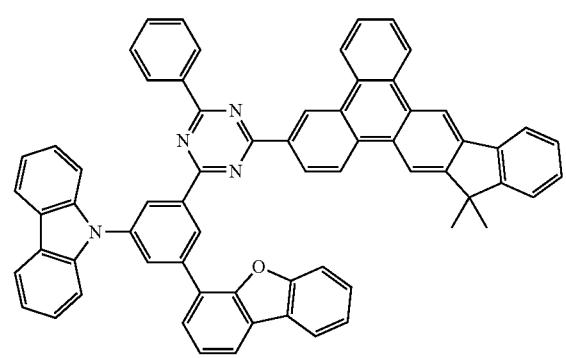
-continued
EX61
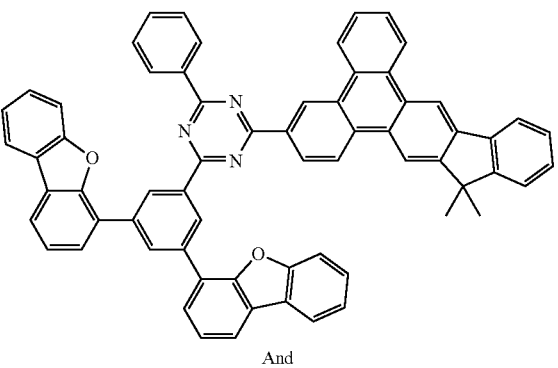
And
EX62
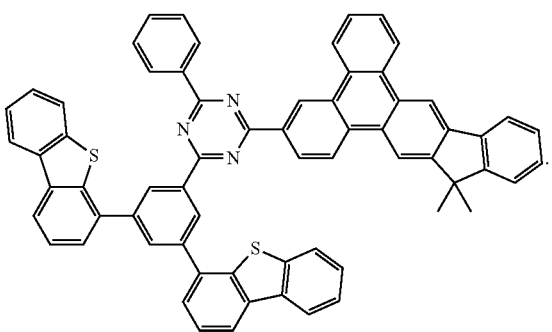
* * * * *